(12) United States Patent
Torgov et al.

(10) Patent No.: US 11,219,689 B2
(45) Date of Patent: Jan. 11, 2022

(54) BORON ENRICHED LINKER ("BEL") COMPOSITIONS FOR BORON NEUTRON CAPTURE THERAPY AND METHODS THEREOF

(71) Applicant: TAE Life Sciences, Foot Hill Ranch, CA (US)

(72) Inventors: Michael Y. Torgov, Redondo Beach, CA (US); Tioga J. Martin, Los Angeles, CA (US)

(73) Assignee: TAE Life Sciences, LLC, Foothill Ranch, CA (US)

( * ) Notice: Subject to any disclaimer, the term of this patent is extended or adjusted under 35 U.S.C. 154(b) by 0 days.

(21) Appl. No.: 16/602,468

(22) Filed: Oct. 10, 2019

(65) Prior Publication Data
US 2020/0114013 A1    Apr. 16, 2020

Related U.S. Application Data

(60) Provisional application No. 62/766,397, filed on Oct. 16, 2018.

(51) Int. Cl.
*A61K 47/52* (2017.01)
*C07F 5/05* (2006.01)
*A61P 35/00* (2006.01)
*A61K 47/68* (2017.01)

(52) U.S. Cl.
CPC .......... *A61K 47/52* (2017.08); *A61K 47/6889* (2017.08); *A61P 35/00* (2018.01); *C07F 5/05* (2013.01)

(58) Field of Classification Search
CPC ................ A61K 47/6855; A61K 47/52; A61K 41/0095; A61K 47/6849; A61K 47/6889; A61P 35/00; C07F 5/05
See application file for complete search history.

(56) References Cited

U.S. PATENT DOCUMENTS

| | | | |
|---|---|---|---|
| 4,361,544 A | 11/1982 | Goldenberg | |
| 4,824,659 A * | 4/1989 | Hawthorne | A61K 51/1045 424/1.53 |
| 5,492,900 A | 2/1996 | LaHann | |
| 5,877,165 A | 3/1999 | Miura et al. | |
| 5,935,944 A | 8/1999 | LaHann | |
| 6,017,902 A | 1/2000 | Glass et al. | |
| 6,228,362 B1 | 5/2001 | Griffiths et al. | |
| 10,058,621 B2 | 8/2018 | Goldenberg et al. | |
| 10,206,918 B2 | 2/2019 | Govindan et al. | |
| 10,266,605 B2 | 4/2019 | Govindan et al. | |
| 2004/0180057 A1 | 9/2004 | Patel | |
| 2017/0112931 A1 | 4/2017 | Leppanen et al. | |
| 2017/0326236 A1 | 11/2017 | Niu et al. | |
| 2019/0055267 A1 | 2/2019 | Liu et al. | |

OTHER PUBLICATIONS

Persson et al., Cancer Biotherapy and Radiopharmaceuticals, 2007, 22(5), p. 585-596. (Year: 2007).*
Alam, et al., Dicesium N-Succinimidyl 3-(Undecahydo-closo-dodecaboranyldithio) propionate, a Novel Heterobifunctional Boronating Agent, J. Med. Chem. 1985, 28, pp. 522-525.
Alam, et al., Boron Neutron Capture Therapy: Linkage of a Boronated Macromolecule to Monoclonal Antibodies Directed against Tumor . . . , J. Med. Chem. 1989, 32 2326-2330.
Bayer, et al., An Improved Method for the Synthesis of [closo0B12(OH)12]-2, Inorg. Chem. 2004, 43, 2018-2020.
Lambert, et al., Antibody-Drug Conjugates (ADCs) for Personalized Treatment of Solid Tumors: A Review, Adv. Ther. (2017) 34:1015-1035.
Dan, et al., Antibody-Drug Conjugates for Cancer Therapy: Chemistry to Clinical Implications, Pharmaceuticals 2018, 11, 32, doi10.3390/ph11020032.
Wu, et al., Site-Specific Conjugation of Boron-Containing Dendrimers to Anti-EGF Receptor Monoclonal Antibody Cetuximab (IMC-C225) . . . Bioconjugate Chem 2004, 15, pp. 185-194.
Chen, et al., Synthesis and Characterization of Oligomeric nido-Carboranyl Phosphate Diester conjugates to Antibody and Antibody . . . Bioconjugate Chem. May 1994, 557-564.
Grimes, Viewpoints: Chemists on Chemistry—Boron Clusters Come of Age, J. of Chem. Edu., vol. 81, No. 5 May 2004 (pp. 658-672).
Gabel, Boron Clusters in Medicinal Chemistry: Perspectives and Problems, PureAppl.Chem. 2015; 87(2): pp. 173-179.
Tamat, et al., Boronated Monoclonal Antibody 225.28S for Potential Use in Neutron Capture Therapy of Malignent . . . Pigment Cell Res., 2:278-280 (1989).
Goswami, et al., Extensions of the Icosahedral Closomer Structure Using Azide-alkyne Click Reactions, Angew. Chem. Int. Engl. (May 9, 2011); 50(20) 4689-4691.
Jalisatgi, et al., A Convienent Route to Diversely Substituted Icosahedral Closomer Nanoscaffolds, J. Am. Chem. Soc. Aug. 17, 2011; 133(32): 12382-12385.

(Continued)

*Primary Examiner* — Michael G. Hartley
*Assistant Examiner* — Leah H Schlientz
(74) *Attorney, Agent, or Firm* — LOSMP; Shane M. Popp

(57) ABSTRACT

Boron Enriched Linker ("BEL") compositions and methods of making BELs are disclosed herein. Consequently, the BELs can be conjugated to antibodies or antibody fragments to create Antibody Boron Conjugates ("ABCs") to provide a method of treating cancer, immunological disorders and other disease by utilizing a Neutron Capture Therapy modality.

17 Claims, 11 Drawing Sheets

(56) References Cited

OTHER PUBLICATIONS

Goswami, et. al., Synthesis of Vertex-Differentiated Icosahedral closo-Boranes: Polyfunctional Scaffolds for Targeted . . . , J. Org. Chem. Dec. 21, 2012; 77(24): 11333-11338.
Goszczynski, et al., Interactions of Boron Clusters and Thier Derivatives with Serum Albumin, Sci. Reports 7:9800 (Aug. 29, 2017).
Li, et al., A Metabolically Stable Boron-Derived Tyrosine Serves as a Theranostic Agent for Positron . . . Bioconjugate Chem. 2019, 30, 2870-2878.
Cirrone, et al., First Experimental Proof of Proton Boron Capture Therapy (PBCT) to Enhance Protontherapty Effectiveness, Sci. Reports 8:1141 (Jan. 18, 2018).
Wilbur, et al., Reagents for Astatination of Biomolecules . . . Bioconjugate Chem. 2012, 23, pp. 409-420 (Feb. 1, 2012).
Bondarev, et al., Synthesis of [closo-B12(OH)11NH3]-: A New Herterobifunctional Dodecaborance . . . J. Am. Chem. Soc. 2013, 135, 13204-13211.
Primus, et al., Bispecific Antibody Mediated Targeting of nido-Carbornanes to Human Colon Cancer Cells, Bioconjugate Chem. 7, pp. 532-535 (1996).

\* cited by examiner

Figure 1. Chemical Synthesis for Boron Enriched Linker No. 1
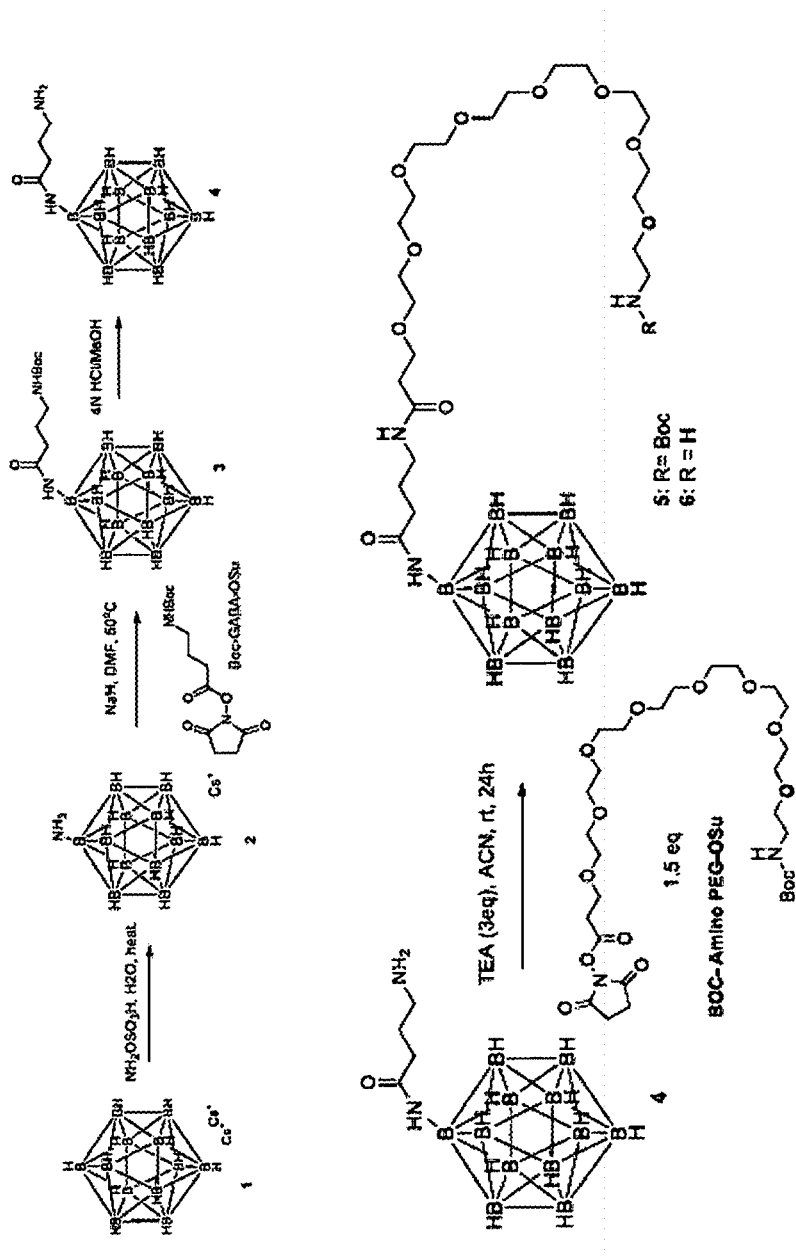

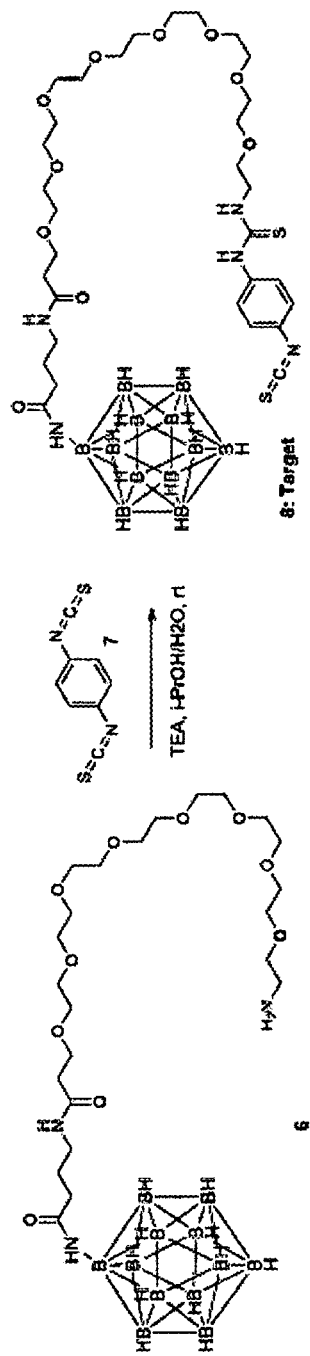
Figure 2. Chemical Synthesis for Boron Enriched Linker No. 1, continued.

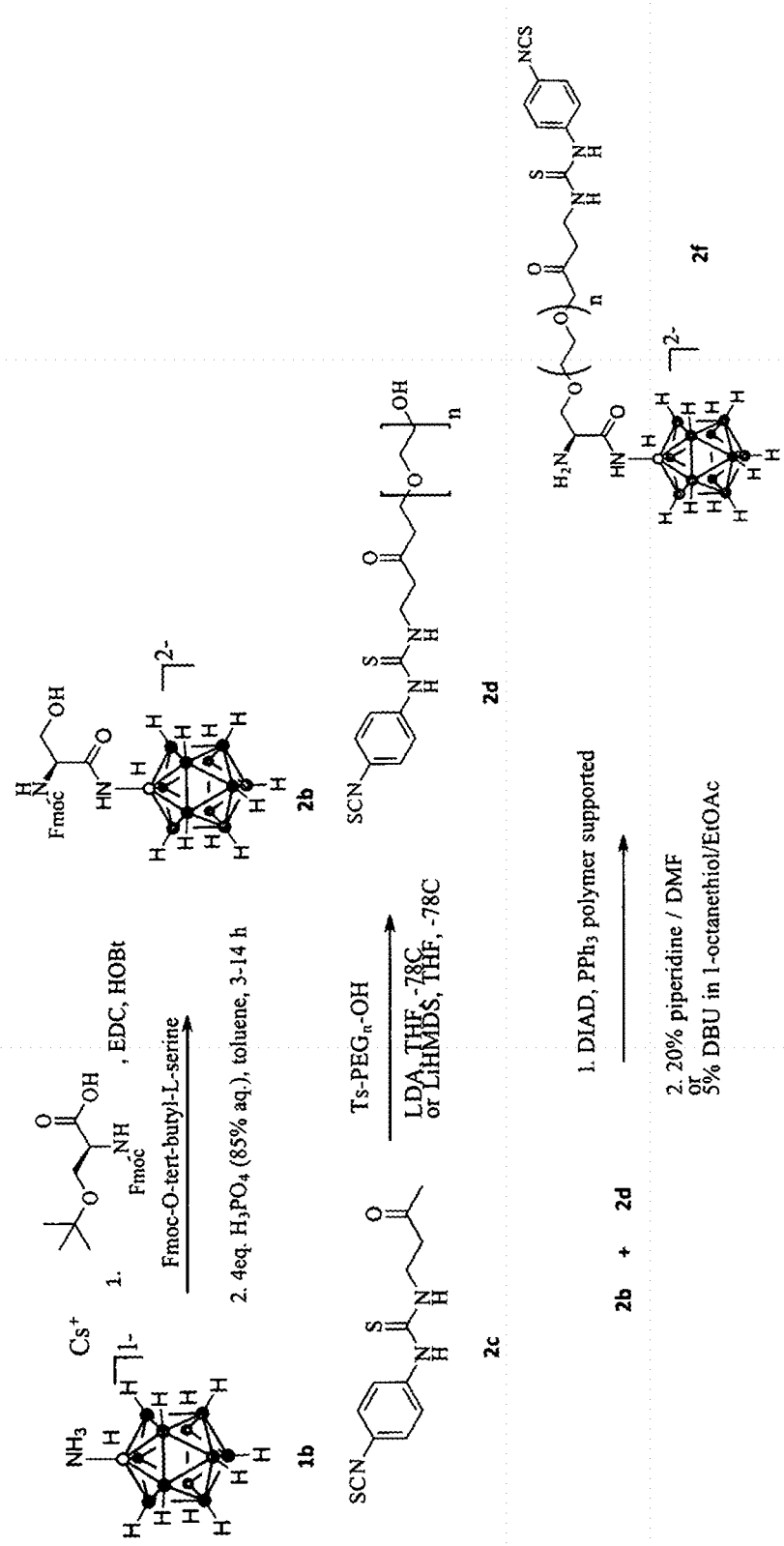
Figure 3. Chemical Synthesis for Boron Enriched Linker No. 2

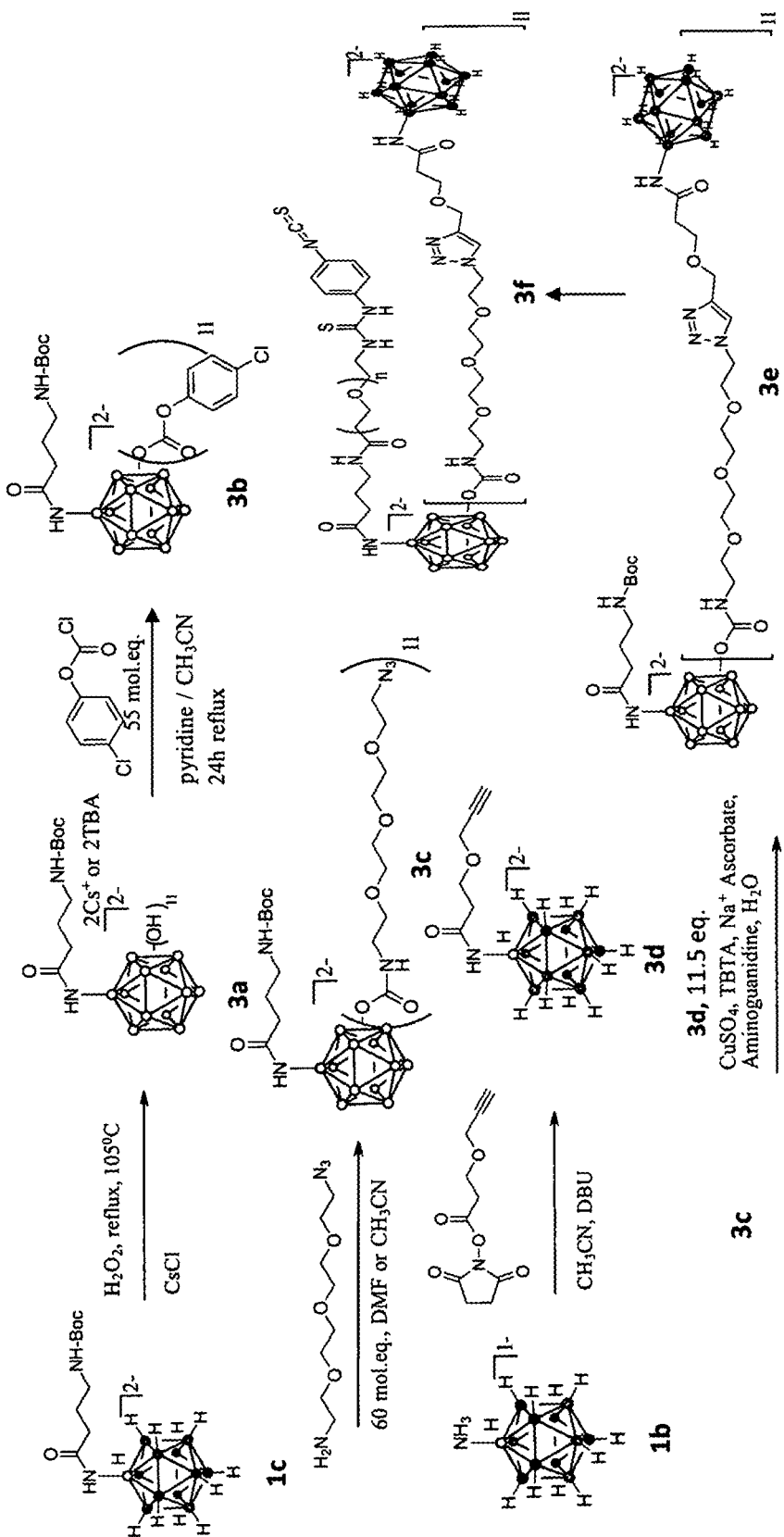
Figure 4. Chemical Synthesis for Boron Enriched Linker No. 3

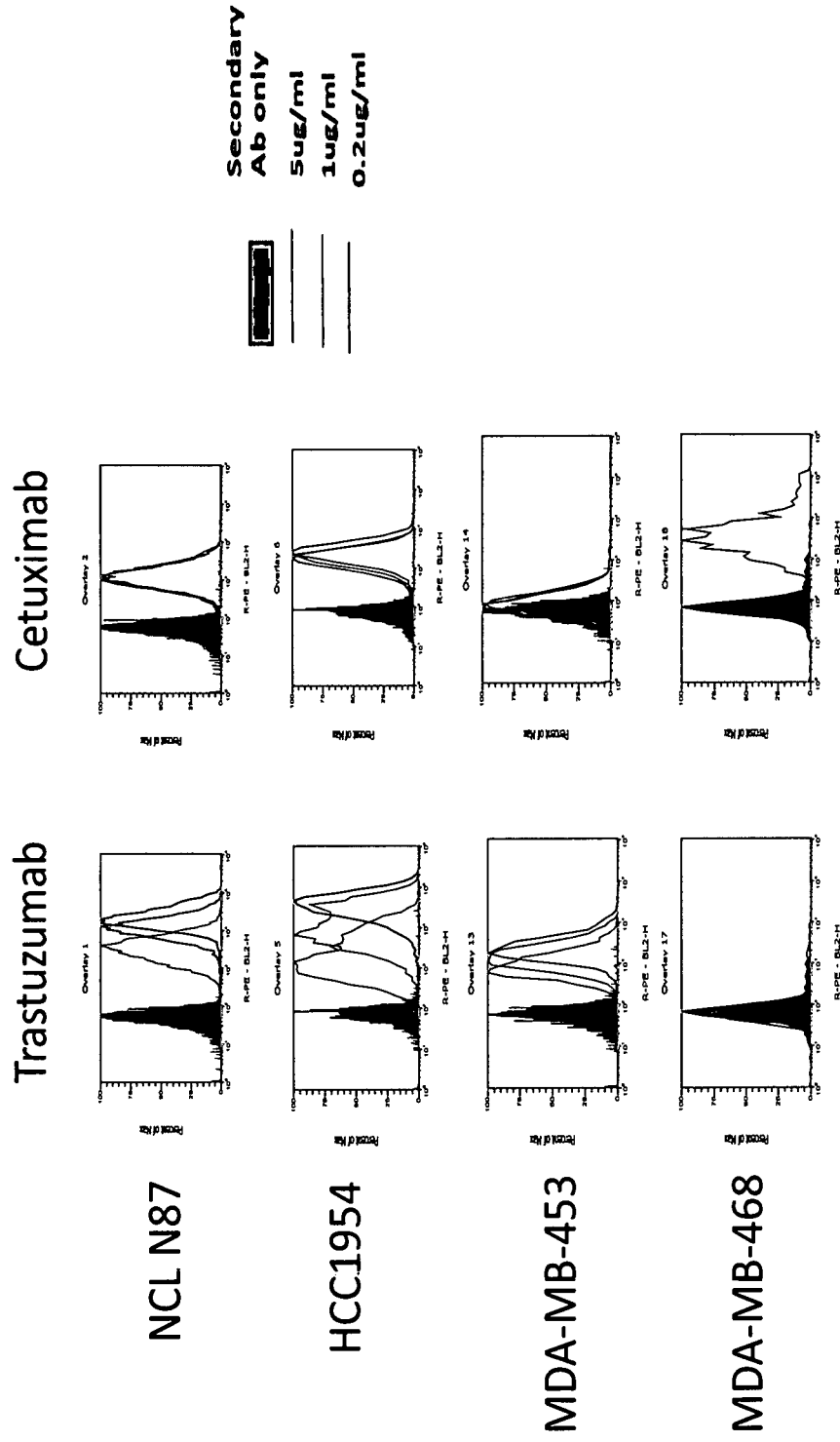
Figure 5. Binding of Trastuzumab and Cetuximab to cancer cell line(s)

Figure 6. Analytical Summary of ABCs Comprising BEL No. 1.

| Antibody boron conjugate | BEL01-Trastuzumab | | | BEL1-Cetuximab | |
|---|---|---|---|---|---|
| Lot | A | B | C | D |
| Conc, mg/mL | 1.44 | 1.1 | 1.5 | 1.4 |
| Boron, µg/mg mAb | 2.3 | 4.3 | 3.3 | 3.7 |
| Linker to Antibody (ICP OES) | 2.5 | 4.8 | 3.7 | 4.2 |
| % Monomer by SEC HPLC | 100% | 100% | 100% | 100% |
| Yield, % | 68% | 58% | 70% | 74% |

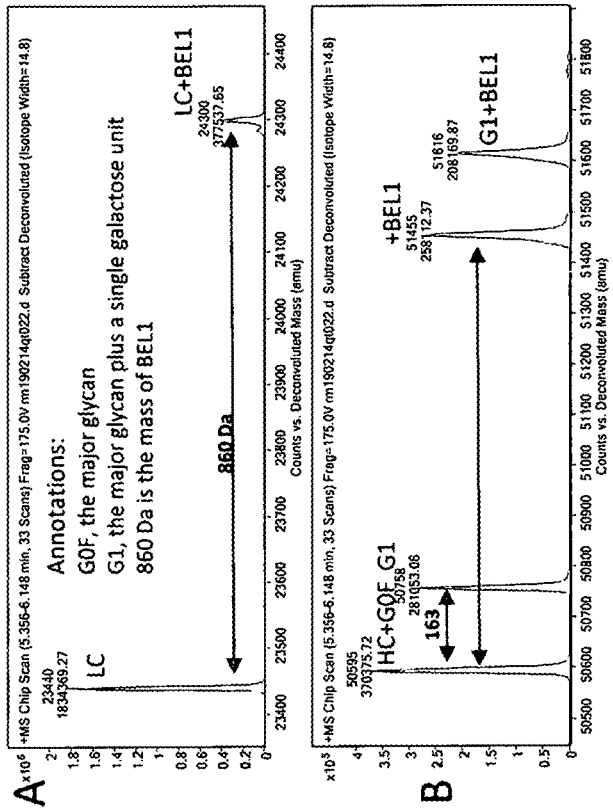
Figure 7. BEL No. 1-Trastuzumab Intact Mass Analysis.

Figure 8. LCMS Analysis & Data Reconciliation.

8A

| Antibody Chain | Predicted MW | Product Found | G0F glycan, Da | Pyro-E, Da | BEL1, Da | CDR Disulfides, Da | Discrepancy, Da |
|---|---|---|---|---|---|---|---|
| LC | 23443.1 | 24300 | n/a | n/a | -860 | +4 | 0.9 |
| HC | 49156.4 | 51455 | -1464.6 | +18 | -860 | +8 | 0.0 |

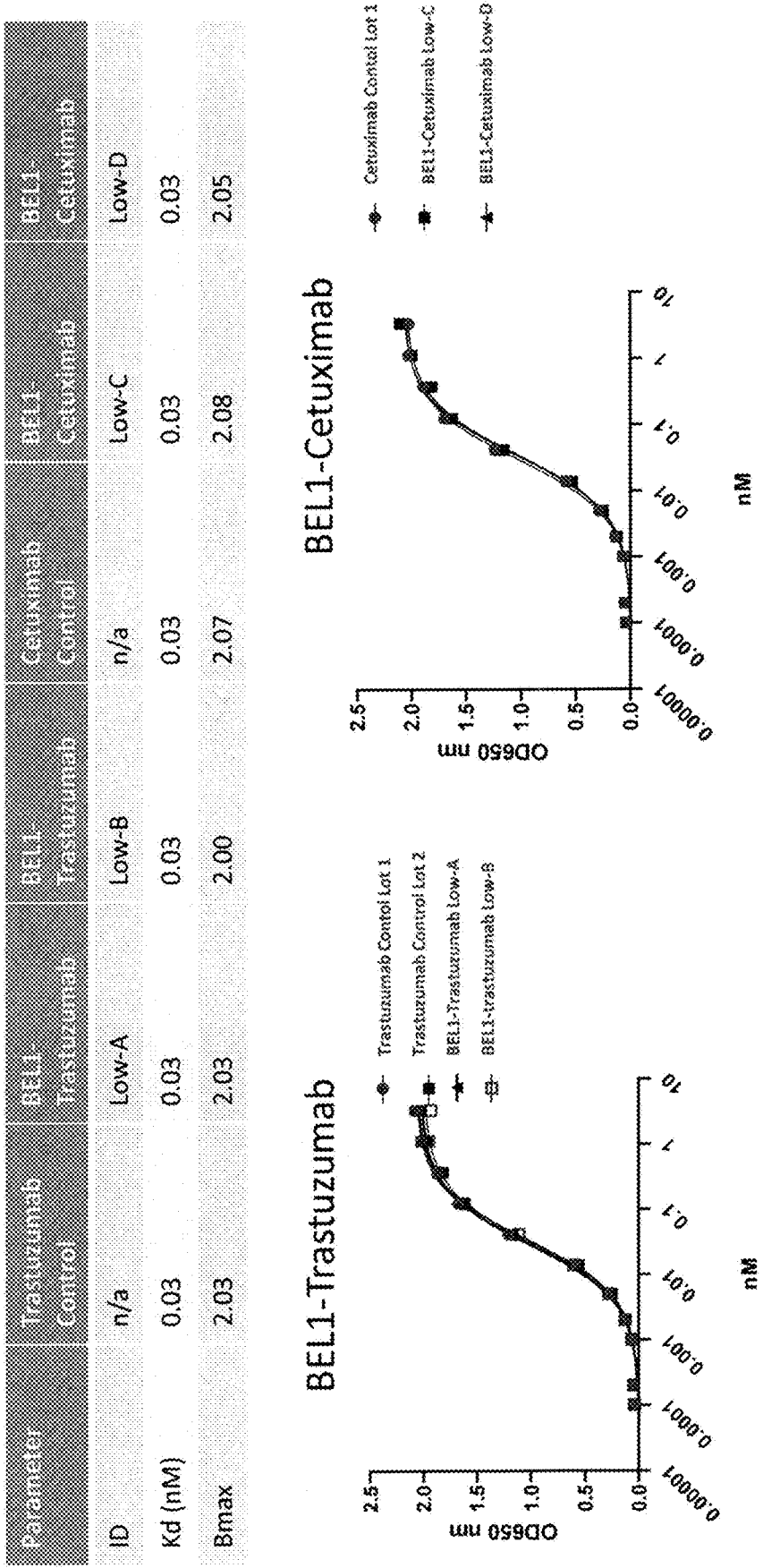
Figure 9. Binding Affinity by ELISA (Low BEL No. 1 Ratio).

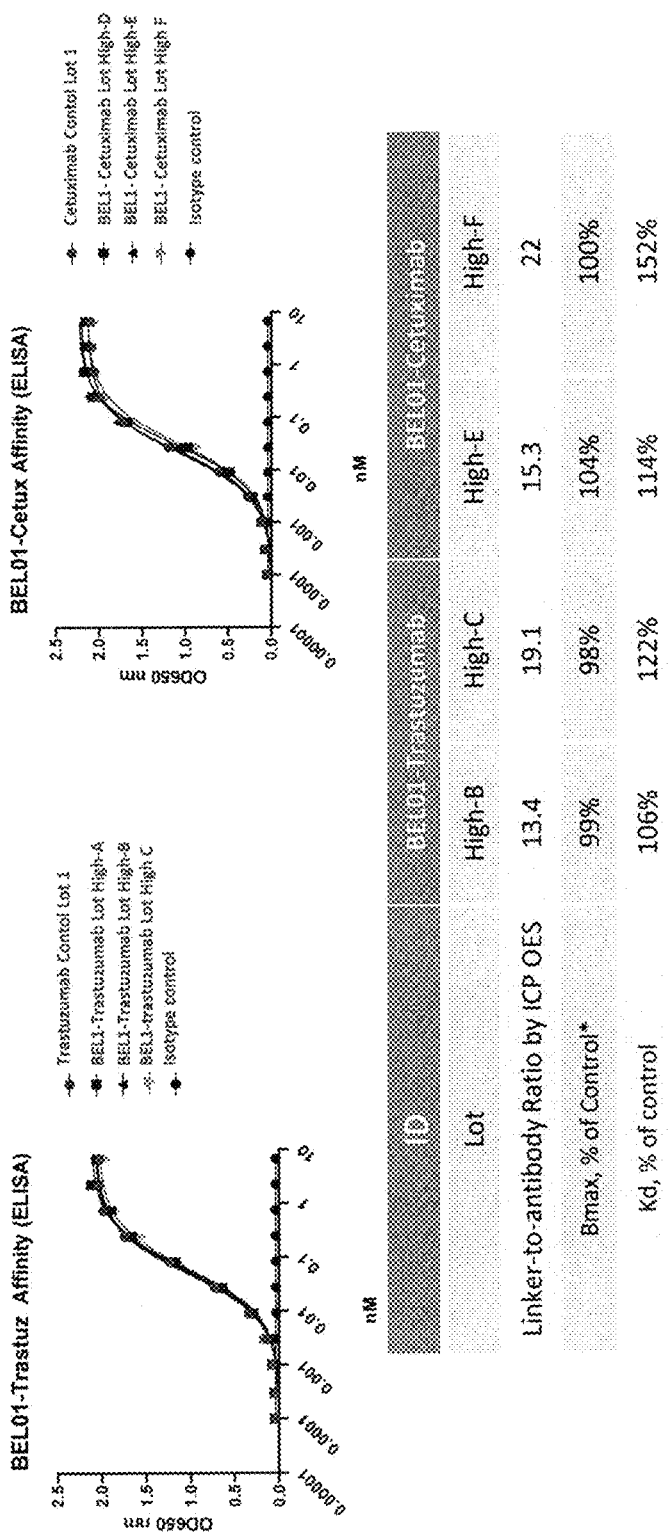
Figure 10. Binding Affinity by ELISA (High BEL No. 1 Ratio).

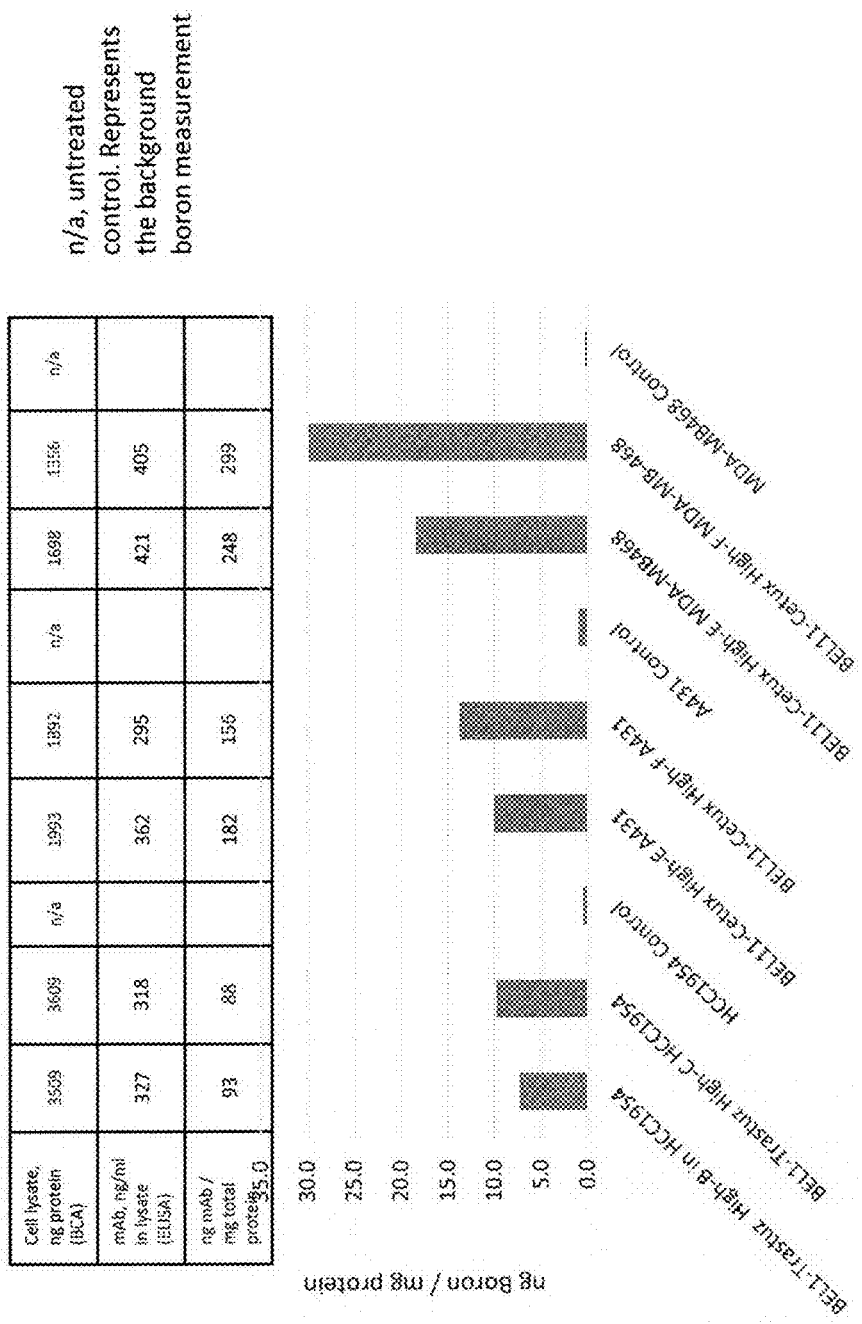
Figure 11. Boron Uptake Study Using High Boron Loaded ABCs.

BORON ENRICHED LINKER ("BEL") COMPOSITIONS FOR BORON NEUTRON CAPTURE THERAPY AND METHODS THEREOF

CROSS-REFERENCE TO RELATED APPLICATIONS

This application claims priority to U.S. Provisional Patent Application No. 62/766,397, filed 16 Oct. 2018. The contents of which are incorporated by reference in their entirety.

STATEMENT OF RIGHTS TO INVENTIONS MADE UNDER FEDERALLY SPONSORED RESEARCH

Not applicable.

FIELD OF THE INVENTION

The invention described herein relates to the field of boron neutron capture therapy (BNCT). Specifically, the invention relates to boron enriched linkers which can be conjugated to a ligand, such as a monoclonal antibody, and used as a vehicle for neutron capture therapy in humans. The invention further relates to the treatment of cancers and other immunological disorders and diseases.

BACKGROUND OF THE INVENTION

Cancer is the second leading cause of death next to coronary disease worldwide. Millions of people die from cancer every year and in the United States alone cancer kills well over a half-million people annually, with over 1.2 million new cases diagnosed per year (American Cancer Society). While deaths from heart disease have been declining significantly, those resulting from cancer generally are on the rise. In the early part of the next century, cancer is predicted to become the leading cause of death unless medical developments change the current trend.

Several cancers stand out as having high rates of mortality. In particular, carcinomas of the lung, prostate, breast, colon, pancreas, ovary, and bladder represent major causes of cancer death. These and virtually all other carcinomas share a common lethal feature in that they metastasise to sites distant from the primary tumor and with very few exceptions, metastatic disease fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients also experience physical debilitations following treatment. Furthermore, many cancer patients experience a recurrence of their disease.

Although cancer therapy has improved over the past decades and survival rates have increased, the heterogeneity of cancer still demands new therapeutic strategies utilizing a plurality of treatment modalities. This is especially true in treating solid tumors at anatomical crucial sites (e.g., glioblastoma, squamous carcinoma of the head and neck and lung adenocarcinoma) which are sometimes limited to standard radiotherapy and/or chemotherapy. Nonetheless, detrimental effects of these therapies are chemo- and radioresistance, which promote loco-regional recurrences, distant metastases and second primary tumors, in addition to severe side-effects that reduce the patients' quality of life.

Neutron Capture Therapy (NCT) is a promising form of radiation therapy. Even though the conceptual techniques of NCT and specifically Boron Neutron Capture Therapy (BNCT) are well known, the technological limitations associated with this type of treatment have slowed progress. However, given the technological improvements in both (i) the infusion or delivery of a capture compound, which preferably concentrates in the tumor, and (ii) the irradiation of the tumor site by neutrons, there has been a resurgence in NCT treatment methods.

From the aforementioned, it will be readily apparent to those skilled in the art that a new treatment paradigm is needed in the treatment of cancers and other immunological diseases. By using modern conjugation modalities and linkers enriched with Boron, a new disease treatment can be achieved with the overall goal of more effective treatment, reduced side effects, and lower production costs.

Given the current deficiencies associated with NCT, it is an object of the present invention to provide new and improved methods of treating cancer(s), immunological disorders, and other diseases utilizing Boron enriched linkers and NCT.

SUMMARY OF THE INVENTION

The invention provides for compositions comprising Boron Enriched Linkers (BELs) synthesized for use as a delivery modality to treat human diseases such as cancer, immunological disorders, including but not limited to rheumatoid arthritis, ankylosing spondylitis, and other cellular diseases, including but not limited to Alzheimer's disease. In certain embodiments, the BELs comprise one or more Boron clusters operably linked to a ligand, such as an antibody to create an Antibody Boron Conjugate (ABC). In a further embodiment, an ABC of the invention comprises a Boron Antibody Ratio (BAR) from about 12 to several hundred or several thousand.

In a further embodiment, the invention comprises methods of concentrating Boron in a cell comprising (i) synthesizing a BEL; conjugating a BEL of the invention to an antibody, creating an antibody boron conjugate (ABC); (ii) administering the ABC to a patient, and (iii) irradiating the cell with neutrons produced in a neutron source.

In another embodiment, the present disclosure teaches methods of synthesizing BELs.

In another embodiment, the present disclosure teaches methods of treating cancer(s), immunological disorders and other diseases in humans.

BRIEF DESCRIPTION OF THE FIGURES

FIG. 1. Chemical Synthesis for Boron Enriched Linker No. 1.

FIG. 2. Chemical Synthesis for Boron Enriched Linker No. 1, continued.

FIG. 3. Chemical Synthesis for Boron Enriched Linker No. 2.

FIG. 4. Chemical Synthesis for Boron Enriched Linker No. 3.

FIG. 5. Binding of Trastuzumab and Cetuximab to cancer cell line(s).

FIG. 6. Analytical Summary of ABCs Comprising BEL No. 1.

FIG. 7. BEL No. 1-Trastuzumab Intact Mass Analysis.

FIG. 8. LCMS Analysis & Data Reconcilitation. FIG. 8A shows the reconciliation of the predicted and observed molecular masses.

FIG. 9. Binding Affinity by ELISA (Low BEL No. 1 Ratio).

FIG. 10. Binding Affinity by ELISA (High BEL No. 1 Ratio).

FIG. 11. Boron Uptake Study Using High Boron Loaded ABCs in cancer cell lines

DETAILED DESCRIPTION OF THE INVENTION

Outline of Sections
I.) Definitions
II.) Antibodies
III.) Boron
  a. Boron Generally
  b. Boron Cluster(s)
IV.) Boron Enriched Linkers (BELs)
  a. The Stretcher Unit
  b. The Spacer Unit
  c. The Bio-Conjugation Handle
  d. Boron Antibody Ratio (BAR)
    i. Lo-BAR
    ii. Hi-BAR
  e. BEL No. 1
  f. BEL No. 2
  g. BEL No. 3
V.) Boron Neutron Capture Therapy
VI.) Methods of Delivering BELs to a Cell
VII.) Methods of Treating Cancer(s) and Other Immunological Disorder(s)
IX.) KITS/Articles of Manufacture

I.) Definitions

Unless otherwise defined, all terms of art, notations and other scientific terms or terminology used herein are intended to have the meanings commonly understood by those of skill in the art to which this invention pertains unless the context clearly indicates otherwise. In some cases, terms with commonly understood meanings are defined herein for clarity and/or for ready reference, and the inclusion of such definitions herein should not necessarily be construed to represent a substantial difference over what is generally understood in the art.

When a trade name is used herein, reference to the trade name also refers to the product formulation, the generic drug, and the active pharmaceutical ingredient(s) of the trade name product, unless otherwise indicated by context.

The terms "advanced cancer", "locally advanced cancer", "advanced disease" and "locally advanced disease" mean cancers that have extended through the relevant tissue capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) cancer.

The term "antibody" is used in the broadest sense unless clearly indicated otherwise. Therefore, an "antibody" can be naturally occurring or man-made such as monoclonal antibodies produced by conventional hybridoma technology. Furthermore, antibodies comprise monoclonal and polyclonal antibodies as well as fragments containing the antigen-binding domain and/or one or more complementarity determining regions of these antibodies. As used herein, the term "antibody" refers to any form of antibody or fragment thereof that specifically binds a target antigen and/or exhibits the desired biological activity and specifically covers monoclonal antibodies (including full length monoclonal antibodies), polyclonal antibodies, multispecific antibodies (e.g., bispecific antibodies), and antibody fragments so long as they specifically bind a target antigen or fragment thereof and/or exhibit the desired biological activity. Any specific antibody can be used in the methods and compositions provided herein. Thus, in one embodiment the term "antibody" encompasses a molecule comprising at least one variable region from a light chain immunoglobulin molecule and at least one variable region from a heavy chain molecule that in combination form a specific binding site for the target antigen. In one embodiment, the antibody is an IgG antibody. For example, the antibody is an IgG1, IgG2, IgG3, or IgG4 antibody. The antibodies useful in the present methods and compositions can be generated in cell culture, in phage, or in various animals, including but not limited to cows, rabbits, goats, mice, rats, hamsters, guinea pigs, sheep, dogs, cats, monkeys, chimpanzees, and apes. Therefore, in one embodiment, an antibody of the present invention is a mammalian antibody. Phage techniques can also be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, ANTIBODY PRODUCTION: ESSENTIAL TECHNIQUES (Wiley, 1997); Shephard, et al., MONOCLONAL ANTIBODIES (Oxford University Press, 2000); Goding, MONOCLONAL ANTIBODIES: PRINCIPLES AND PRACTICE (Academic Press, 1993); and CURRENT PROTOCOLS IN IMMUNOLOGY (John Wiley & Sons, most recent edition).

An antibody of the present invention can be modified by recombinant means to increase efficacy of the antibody in mediating the desired function. Thus, it is within the scope of the invention that antibodies can be modified by substitutions using recombinant means. Typically, the substitutions will be conservative substitutions. For example, at least one amino acid in the constant region of the antibody can be replaced with a different residue. See, e.g., U.S. Pat. Nos. 5,624,821, 6,194,551, Application No. WO 9958572; and Angal, et al., Mol. Immunol. 30: 105-08 (1993). The modification in amino acids includes deletions, additions, and substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to normal or defective 158P1D7. See e.g., ANTIBODY ENGINEERING: A PRACTICAL APPROACH (Oxford University Press, 1996). Suitable antibodies with the desired biologic activities can be identified using the following in vitro assays including but not limited to: proliferation, migration, adhesion, soft agar growth, angiogenesis, cell-cell communication, apoptosis, transport, signal transduction, and the following in vivo assays such as the inhibition of tumor growth. The antibodies provided herein can also be useful in diagnostic applications. As capture or non-neutralizing antibodies, they can be screened for the ability to bind to the specific antigen without inhibiting the receptor-binding or biological activity of the antigen. As neutralizing antibodies, the antibodies can be useful in competitive binding assays.

The term "antigen-binding portion" or "antibody fragment" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')2 fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarily determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

As used herein, any form of the "antigen" can be used to generate an antibody that is specific for the target. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may be genomic or non-genomic (e.g., cDNA) and encodes at least a portion of the extracellular domain. As used herein, the term "portion" refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids. In one embodiment, the antibody of the methods and compositions herein specifically bind at least a portion of the extracellular domain of the target of interest.

"Antibody Boron Conjugate ("ABC") is an important class of biopharmaceutical drugs designed as a targeted therapy to enhance Boron Neutron Capture Therapy (BNCT). Unlike ADCs, which consist of antibodies combined with a toxic payload, ABCs are made up of an antibody, or antibody fragment, conjugated with a non-cytotoxic, boron containing molecule such as a Boron Enriched Linker (BEL). It is not until the boron in the ABC is irradiated with epithermal neutrons in a BNCT treatment that it releases a cell killing alpha particle. This type of treatment is currently used in cancer treatment and may also be a suitable for other disease indications. In contrast to chemotherapy and ADC treatment, targeted BNCT using ABCs has the potential to kill only the cancer cells and spare healthy cells. Antibody Boron Conjugates are examples of bioconjugates and immunoconjugates.

"Bispecific" antibodies are also useful in the present methods and compositions. As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al., Nature 305:537-39 (1983). Alternatively, bispecific antibodies can be prepared using chemical linkage. See, e.g., Brennan, et al., Science 229:81 (1985). Bispecific antibodies include bispecific antibody fragments. See, e.g., Hollinger, et al., Proc. Natl. Acad. Sci. U.S.A. 90:6444-48 (1993), Gruber, et al., J. Immunol. 152:5368 (1994).

"Boron Antibody Ratio" (BAR) means the average number of boron atoms conjugated to the antibodies on the creation of antibody boron conjugates (ABCs) using boron enriched linkers (BELs). This is an important attribute of ABCs as the number of borons carried by an antibody, or antibody fragment, and delivered to the tumor cell will directly influence its effectiveness as a treatment. This is because the BAR value affects the efficacy of the drug, as low drug loading reduces the potency, while high drug loading may negatively affect manufacturing properties and pharmacokinetics. For the purposes of this disclosure, the conjugation chemistry taught herein includes, but not is limited to, lysine side-chain amidation or cysteine interchain disulfide bond reduction based, resulting in a low BAR (12-60 boron atoms) (Lo-BAR) or a high BAR (>100 boron atoms) (Hi-BAR) can be achieved depending on the design of the BEL being utilized in the conjugation.

"Boron Enriched Linker (BEL) means a component of an Antibody Boron Conjugate (ABC). These are linkers designed to contain a pre-defined number of boron molecules to be used to generate ABCs with a pre-determined number of boron molecules to give a low boron to antibody ratio (lo-BAR) or a high boron to antibody ration (hi-BAR). BELs can be synthesized in multiple formats depending on the number of boron molecules required for attachment to the final ABC. They can be made with either cleavable or non cleavable linkers and the linkers can be of multiple lengths depending on the ABC requirements and treatment target.

The term "compound" refers to and encompasses the chemical compound (e.g. a BEL) itself as well as, whether explicitly stated or not, and unless the context makes clear that the following are to be excluded: amorphous and crystalline forms of the compound, including polymorphic forms, where these forms may be part of a mixture or in isolation; free acid and free base forms of the compound, which are typically the forms shown in the structures provided herein; isomers of the compound, which refers to optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc. forms; salts of the compound, preferably pharmaceutically acceptable salts, including acid addition salts and base addition salts, including salts having organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different. In some instances, reference made herein to a compound of the invention will include an explicit reference to one or of the above forms, e.g., salts and/or solvates; however, this reference is for emphasis only, and is not to be construed as excluding other of the above forms as identified above The terms "inhibit" or "inhibition of" as used herein means to reduce by a measurable amount, or to prevent entirely.

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic cancer" and "metastatic disease" mean cancers that have spread to regional lymph nodes or to distant sites, and are meant to include stage D disease under the AUA system and stage T×N×M+ under the TNM system.

"Molecular recognition" means a chemical event in which a host molecule is able to form a complex with a second molecule (i.e. the guest). This process occurs through non-covalent chemical bonds, including but not limited to, hydrogen bonding, hydrophobic interactions, ionic interaction.

"Pharmaceutically acceptable" refers to a non-toxic, inert, and/or composition that is physiologically compatible with humans or other mammals.

"Polyhedral Skeletal Electron Pair Theory (PSEPT) means a set of widely accepted electron counting rules useful for predicting the structure of clusters such as borane. The electron counting rules were originally formulated by Kenneth Wade and are sometimes referred to as Wade's rules.

The term "neutron capture agent" means a stable non-reactive chemical isotope which, when activated by neutrons produces alpha-rays and gamma-rays.

The term "neutron capture therapy" means a noninvasive therapeutic modality for treating locally invasive malignant tumors such as primary brain tumors and recurrent head and neck cancer and other immunological disorders and disease by irradiating a neutron capture agent with neutrons.

As used herein, the terms "specific", "specifically binds" and "binds specifically" refer to the selective binding of the antibody to the target antigen epitope. Antibodies can be tested for specificity of binding by comparing binding to appropriate antigen to binding to irrelevant antigen or antigen mixture under a given set of conditions. If the antibody binds to the appropriate antigen at least 2, 5, 7, and preferably 10 times more than to irrelevant antigen or antigen mixture then it is considered to be specific. In one embodiment, a specific antibody is one that only binds the target antigen, but does not bind to the irrelevant antigen. In another embodiment, a specific antibody is one that binds a human target antigen but does not bind a non-human target antigen with 70%, 75%, 80%, 85%, 90%, 91%, 92%, 93%, 94%, 95%, 96%, 97%, 98%, 99% or greater amino acid homology with the human target antigen. In another embodiment, a specific antibody is one that binds a human target antigen and binds a murine target antigen, but with a higher degree of binding the human antigen. In another embodiment, a specific antibody is one that binds a human target antigen and binds a primate target antigen, but with a higher degree of binding the human target antigen. In another embodiment, the specific antibody binds to a human target antigen and any non-human target antigen, but with a higher degree of binding the human antigen or any combination thereof.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; as is readily appreciated in the art, full eradication of disease is a preferred but albeit not a requirement for a treatment act.

"zwitter-ion" means a molecule with two or more functional groups, of which at least one has a positive and one has a negative electric charge whereby the net charge of the entire molecule is zero. Zwitter-ion is formerly known as a dipolar ion.

II.) Antibodies

Another aspect of the invention provides antibodies conjugated to BELs of the invention. These antibodies of the invention are particularly useful in cancer prognostic assays, imaging, diagnostic, and therapeutic methodologies. Similarly, such antibodies are useful in the treatment, and/or prognosis of bladder, pancreas, ovarian, head and neck and other cancers, to the extent the target antigen is also expressed or overexpressed in these other cancers. Moreover, antibodies of the invention are therapeutically useful in treating cancers in which the expression of the target antigen is involved and when the antibodies are conjugated to a BEL of the invention as described herein.

Various methods for the preparation of antibodies, specifically monoclonal antibodies, are well known in the art. For example, antibodies can be prepared by immunizing a suitable mammalian host using a target related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of the target can also be used, such as a Target GST-fusion protein. In a particular embodiment, a Target GST fusion protein comprising all or most of the amino acid sequence of the Target is produced, and then used as an immunogen to generate appropriate antibodies.

In addition, naked DNA immunization techniques known in the art are used (with or without purified Target-related protein or expressing cells) to generate an immune response to the encoded immunogen (for review, see Donnelly et al., 1997, Ann. Rev. Immunol. 15: 617-648).

The amino acid sequence of a target protein can be analyzed to select specific regions of the target protein for generating antibodies. For example, hydrophobicity and hydrophilicity analyses of a target amino acid sequence are used to identify hydrophilic regions in the target structure.

Regions of a target protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Hydrophilicity profiles can be generated using the method of Hopp, T. P. and Woods, K. R., 1981, Proc. Natl. Acad. Sci. U.S.A. 78:3824-3828. Hydropathicity profiles can be generated using the method of Kyte, J. and Doolittle, R. F., 1982, J. Mol. Biol. 157:105-132. Percent (%) Accessible Residues profiles can be generated using the method of Janin J., 1979, Nature 277:491-492. Average Flexibility profiles can be generated using the method of Bhaskaran R., Ponnuswamy P. K., 1988, Int. J. Pept. Protein Res. 32:242-255. Beta-turn profiles can be generated using the method of Deleage, G., Roux B., 1987, Protein Engineering 1:289-294. Thus, each region identified by any of these programs or methods is within the scope of the present invention. Preferred methods for the generation of target antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a target immunogen is often conducted by injection over a suitable time period and with use of a suitable adjuvant, as is understood in the art. During the immunization schedule, titers of antibodies can be taken to determine adequacy of antibody formation.

Target specific monoclonal antibodies can be produced by various means well known in the art. For example, immortalized cell lines that secrete a desired monoclonal antibody are prepared using the standard hybridoma technology of Kohler and Milstein or modifications that immortalize antibody-producing B cells, as is generally known. Immortalized cell lines that secrete the desired antibodies are screened by immunoassay in which the antigen is a Target-related protein. When the appropriate immortalized cell culture is identified, the cells can be expanded and antibodies produced either from in vitro cultures or from ascites fluid.

The antibodies or fragments of the invention can also be produced by recombinant means. Regions that bind specifically to the desired regions of a Target protein can also be produced in the context of chimeric or complementarity-determining region (CDR) grafted antibodies of multiple species origin. Humanized or human antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al., 1986, Nature 321: 522-525; Riechmann et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296.

In a preferred embodiment, the antibodies of the present invention comprise fully human antibodies (Target mAbs). Various methods in the art provide means for producing fully human Target mAbs. For example, a preferred embodiment provides for techniques using transgenic mice, inactivated for antibody production, engineered with human heavy and light chains loci referred to as Xenomouse (Amgen Fremont, Inc.). An exemplary description of preparing transgenic mice that produce human antibodies can be found in U.S. Pat. No. 6,657,103. See, also, U.S. Pat. Nos. 5,569,825; 5,625,126; 5,633,425; 5,661,016; and 5,545,806; and Mendez, et. al. Nature Genetics, 15: 146-156 (1998); Kellerman, S. A. & Green, L. L., Curr. Opin. Biotechnol 13, 593-597 (2002).

In addition, human antibodies of the invention can be generated using the HuMAb mouse (Medarex, Inc.) which contains human immunoglobulin gene miniloci that encode unrearranged human heavy (mu and gamma) and kappa light chain immunoglobulin sequences, together with targeted mutations that inactivate the endogenous mu and kappa chain loci (see e.g., Lonberg, et al. (1994) Nature 368(6474): 856-859).

In another embodiment, fully human antibodies of the invention can be raised using a mouse that carries human immunoglobulin sequences on transgenes and transchromosomes, such as a mouse that carries a human heavy chain transgene and a human light chain transchromosome. Such mice, referred to herein as "KM mice", such mice are described in Tomizuka et al. (2000) Proc. Natl. Acad. Sci. USA 97:722-727 and PCT Publication WO 02/43478 to Tomizuka, et al.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Human monoclonal antibodies of the invention can also be prepared using mice into which genomic sequences bearing endogenous mouse variable segments at the immunoglobulin heavy chain (VH, DH, and JH segments) and/or kappa light chain (VK and JK) loci have been replaced, in whole or in part, with human genomic sequences bearing unrearranged germline variable segments of the human immunoglobulin heavy chain (VH, DH, and JH) and/or kappa light chain (VK and JK) loci (Regeneron, Tarrytown, N.Y.). See, for example, U.S. Pat. Nos. 6,586,251, 6,596, 541, 7,105,348, 6,528,313, 6,638,768, and 6,528,314.

In another embodiment, the Target mAb or antigen binding portion thereof competes for binding with an antibody having such heavy and/or light chain CDR(s).

Engineered antibodies of the invention include those in which modifications have been made to framework residues within VH and/or VL (e.g. to improve the properties of the antibody). Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis (e.g., "backmutated" from leucine to methionine). Such "backmutated" antibodies are also intended to be encompassed by the invention.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 2003/0153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, a Target mAb of the invention may be chemically modified (e.g., one or more chemical moieties can be attached to the antibody) or be modified to alter its glycosylation, again to alter one or more functional properties of the mAb. Each of these embodiments is described in further detail below.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the Target mAb.

In another embodiment, the Fc hinge region of an antibody is mutated to decrease the biological half life of the Target mAb. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the Target mAb is modified to increase its biological half life. Various approaches are possible. For example, mutations can be introduced as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the Target mAb. For example, one or more amino acids selected from amino acid specific residues can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

Reactivity of Target antibodies with a Target-related protein can be established by a number of well known means, including Western blot, immunoprecipitation, ELISA, and FACS analyses using, as appropriate, Target-related proteins, Target-expressing cells or extracts thereof. A Target mAb or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bispecific antibodies specific for two or more target epitopes are generated using methods generally known in the art. Homodimeric antibodies can also be generated by cross-linking techniques known in the art (e.g., Wolff et al., Cancer Res. 53: 2560-2565).

One of ordinary skill in the art will appreciate and be enabled to make variations and modifications to the disclosed embodiment without altering the function and purpose of the invention disclosed herein. Such variations and modifications are intended within the scope of the present disclosure.

III.) Boron (a.) Boron Generally

Generally speaking and for purposes of this disclosure, Boron is a chemical element with symbol B and atomic number 5. Primarily used in chemical compounds, natural boron is composed of two stable isotopes, once of which is Boron-10 and the other is Boron-11. Boron-10 isotope is useful for capturing thermal neutrons, which makes it a promising tool in a therapeutic context using Boron Neutron Capture Therapy. Biologically, elemental boron, boron oxide, boric acid, boron-10, and boron-11 are relatively nontoxic to humans and animals (with toxicity similar to that of table salt). Based on the foregoing, it will be readily apparent to one of skill in the art that improved modalities for providing high concentrations of boron into a cancer cell are advantageous. It is an object of the present disclosure to provide that advantage.

(b.) Boron Cluster(s)

Boron clusters or Boranes is the name given to the class of synthetic hydrides of boron with a generic formula $B_xH_y$. The molecules of these compounds are electron deficient and so are highly reactive with respect to electron-pair donors. The boranes belong to a class of cluster compounds which have been the subject of developments in chemical bonding theory. For example, polyhedral skeletal electron pair theory (PSEPT), also referred to as Wade's rules provides electron counting rules useful for predicting the structure of clusters. Briefly, different rules (4n, 5n, or 6n) are invoked depending on the number of electrons per vertex. For example, The 4n rules are reasonably accurate in predicting the structures of clusters having about 4 electrons per vertex, as is the case for many boranes and carboranes. For such clusters, the structures are based on deltahedra, which are polyhedra in which every face is triangular. The 4n clusters are classified as closo-, nido-, arachno- or hypho-, based on whether they represent a complete (closo-) deltahedron, or a deltahedron that is missing one (nido-), two (arachno-) or three (hypho-) vertices. However, hypho clusters are relatively uncommon due to the fact that the electron count is high enough to start to fill antibonding orbitals and destabilize the 4n structure. If the electron count is close to 5 electrons per vertex, the structure often changes to one governed by the 5n rules, which are based on 3-connected polyhedra. As the electron count increases further, the structures of clusters with 5n electron counts become unstable, so the 6n rules can be implemented. The 6n clusters have structures that are based on rings. A molecular orbital treatment can be used to rationalize the bonding of cluster compounds of the 4n, 5n, and 6n types. In one embodiment the disclosure teaches the use of boron clusters in synthesizing a Boron Enriched Linker ("BEL") comprising the boron clusters set forth in Table I. In a preferred embodiment, boron clusters of the disclosure comprise a 4n cluster. The polyhedral set forth in Table I are closo polyhedra, and are the basis for the 4n rules discussed, supra. The number of vertices in the cluster determines what polyhedron the structure is based on. In a further preferred embodiment a boron cluster of the disclosure comprises a closo (4n+2) structure. In one embodiment of the present disclosure, the boron cluster is set forth in Table I(A).

III.) Boron Enriched Linkers ("BELs")

It is an object of the present invention to provide boron enriched linkers ("BEL" or "BELs" as the context necessitates) to be to conjugated to an antibody or fragment thereof whereby the BEL comprises a plurality of modified boron clusters of the invention to create an antibody boron conjugate (ABC). As discussed, infra, ABCs of the present invention are used as a modality to provide concentrated amounts of boron to a cancer cell as a precursor for BNCT.

Generally speaking, a BEL of the disclosure comprises a linker attached to a boron containing cluster using a suitable linker attachment handle. For example, see BONDAREV, et. al, J. Am. Chem. Soc., 201(3) 13204-13211 (2013). The boron cluster is then used as a branching point for the addition of a plurality of boron clusters linked in a daisy chain fashion. The BELs of the present disclosure are designed with two (2) primary principles in mind. First, the BELs are designed to assess various modes of bio-conjugation known in the art, each of which is included within the scope of the present disclosure. Second, the BEL should endeavor to incorporate charged entities (e.g. lysine, primary amines, or quaternary amines) which shall render the BEL a zwitter-ion, thus effectively reducing the net negative charge.

In one embodiment, the BEL of the present invention comprises a linker of the following formula:

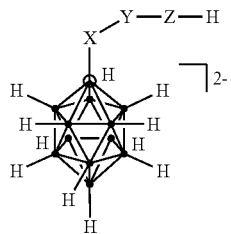

Whereby X is the functionalization at the vertex and is selected from the group consisting of $NH_3$, SH, or OH which creates a mono-substituted boronate.
Y=a Stretcher Unit;
Z=a Spacer Unit; and/or
H=a bioconjugation handle (A) The Stretcher Unit The Stretcher unit (Y), when present, is capable of linking an Antibody unit to a Spacer unit (—Z—), if present; or to a Boron cluster unit (—B). Useful functional groups that can be present on a mAb of the invention, either naturally or via chemical manipulation include, but are not limited to, sulfhydryl, amino, hydroxyl, the anomeric hydroxyl group of a carbohydrate, and carboxyl. Suitable functional groups are sulfhydryl and amino acids. In one example, sulfhydryl groups can be generated by reduction of the intramolecular disulfide bonds of a mAb. In another embodiment, sulfhydryl groups can be generated by reaction of an amino group of a lysine moiety of a mAb with 2-iminothiolane (Traut's reagent) or other sulfhydryl generating reagents. In certain embodiments, the mAb is a recombinant antibody and is engineered to carry one or more lysines. In certain other embodiments, the recombinant mAb is engineered to carry additional sulfhydryl groups, e.g., additional cysteines. In one embodiment, the Stretcher unit forms a bond with a sulfur atom of the Antibody unit. The sulfur atom can be derived from a sulfhydryl group of an antibody.

In certain embodiments, the Stretcher unit is linked to the Antibody unit via a disulfide bond between a sulfur atom of the Antibody unit and a sulfur atom of the Stretcher unit.

In yet other embodiments, the Stretcher contains a reactive site that can form a bond with a primary or secondary amino group of an Antibody. Examples of these reactive sites include, but are not limited to, activated esters such as succinimide esters, 4 nitrophenyl esters, pentafluorophenyl esters, tetrafluorophenyl esters, anhydrides, acid chlorides, sulfonyl chlorides, isocyanates and isothiocyanates.

In some embodiments, the Stretcher contains a reactive site that is reactive to a modified carbohydrate's (—CHO) group that can be present on an Antibody. For example, a carbohydrate can be mildly oxidized using a reagent such as sodium periodate and the resulting (—CHO) unit of the oxidized carbohydrate can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko et al., 1991, *Bioconjugate Chem.* 2:133-41, or quinolinone, such as those described by Qiang, 2013, JACS 135:4996-99

In a preferred embodiment, the Stretcher Unit is chosen from a carboxylic acid and its derivatives, alcohols, aliphatic carbon chains, and di-peptide or tri-peptide amino acids.

(B) The Spacer Unit

The Spacer unit (—Z—), when present, links a Stretcher Unit to the Antibody unit when a Stretcher unit is present. Alternately, the Spacer unit links the Antibody unit to the Boron Cluster unit when the Stretcher unit is absent. Spacer units are of two general types: non self-immolative or self-immolative. A non self-immolative Spacer unit is one in which part or all of the Spacer unit remains bound to the Boron Cluster moiety after cleavage, particularly enzymatic, of an Antibody unit from the antibody boron conjugate. Examples of a non self-immolative Spacer unit include, but are not limited to a (glycine-glycine) Spacer unit and a glycine Spacer unit. When an ABC containing a glycine-glycine Spacer unit or a glycine Spacer unit undergoes enzymatic cleavage via an enzyme (e.g., a tumor-cell associated-protease, a cancer-cell-associated protease or a lymphocyte-associated protease), a glycine-glycine-Boron moiety or a glycine-Boron moiety is cleaved from the Antibody. In one embodiment, an independent hydrolysis reaction takes place within the target cell, cleaving the glycine-Drug moiety bond and liberating the Boron Cluster.

In some embodiments, a non self-immolative Spacer unit (—Y—) is -Gly-. In some embodiments, a non self-immolative Spacer unit (—Y—) is -Gly-Gly-.

In one embodiment, an ABC is provided in which the Spacer unit is absent (y=0), or a pharmaceutically acceptable salt or solvate thereof.

In some embodiments, —Y— is a p-aminobenzyl alcohol (PAB) unit whose phenylene portion is substituted with $Q_m$ wherein Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; and m is an integer ranging from 0-4. The alkyl, alkenyl and alkynyl groups, whether alone or as part of another group, can be optionally substituted.

In some embodiments, —Y— is a PAB group that is linked to —$W_w$— via the amino nitrogen atom of the PAB group, and connected directly to -D via a carbonate, carbamate or ether group as described by Toki et al., 2002, *J. Org. Chem.* 67:1866-1872.

Other examples of self-immolative spacers include, but are not limited to, aromatic compounds that are electronically similar to the PAB group such as 2-aminoimidazol-5-methanol derivatives (Hay et al., 1999, *Bioorg. Med. Chem. Lett.* 9:2237) and ortho or para-aminobenzylacetals. Spacers can be used that undergo cyclization upon amide bond hydrolysis, such as substituted and unsubstituted 4-aminobutyric acid amides (Rodrigues et al., 1995, *Chemistry Biology* 2:223), appropriately substituted bicyclo[2.2.1] and bicyclo[2.2.2] ring systems (Storm et al., 1972, *J. Amer. Chem. Soc.* 94:5815) and 2-aminophenylpropionic acid amides (Amsberry et al., 1990, *J. Org. Chem.* 55:5867). Elimination of amine-containing drugs that are substituted at the α-position of glycine (Kingsbury et al., 1984, *J. Med. Chem.* 27:1447) are also examples of self-immolative spacers.

In a preferred embodiment, the Spacer Unit is selected from the group consisting of an aliphatic chain (preferred range from C3-C8), a fatty acid, or a PEG (ranging from 3-12).

(C) The Bio-Conjugation Handle

The bioconjugation handle (—H—) of the present invention comprises phenyl isothiocyanate, malemide, succinamide, dibromomaleimide, dithiophenolmaleimide, azide, propargyl, dibenzocyclooctyne or oxiamine and allows for the conjugation of the BEL to a mAb of the invention or to additional BELs.

(D) Boron Antibody Ratio (BAR)

The disclosure provides a new modality for providing boron to a cell for the use of BNCT via an Antibody Boron Conjugate (ABC). An ABC of the present disclosure furthers traditional conjugation chemistry paradigms by allowing significant amounts of Boron to be concentrated into a cell. This is the crucial first step needed to enhance common BNCT treatment paradigms. In order to measure the amount of Boron in an ABC relative to the antibody to which is it conjugated, the inventors have utilized a ratio known as the Boron-Antibody Ratio (BAR). Briefly, the BAR represents the average number of Boron clusters conjugated to a particular antibody. The BAR represents an important attribute to an ABC. For example, the BAR value affects the stability of the mAb as well as the overall stability of the ABC. In addition, from a treatment perspective, in order to enhance the efficacy of the BNCT, the ability to deliver a high concentration of Boron to a cancer cell is advantageous.

In one aspect of the present disclosure, a BAR of 12 to 60 is within the scope of the invention. In another embodiment, a BAR of 144-720 is within the scope of the invention. In one embodiment an ABC with a BAR from about 2-1000 is within the scope of the present invention.

(i) Lo-BAR

Conjugates that carry up to 100 of boron atoms, and are expected to deliver the amount of boron that is insufficient for the efficient neutron capture and may not lead to cancer cell death (ii) Hi-BAR Conjugates that carry greater than 100 of boron atoms, and are expected to deliver the amount of boron above and beyond of what is minimally required for the efficient neutron capture, and will lead to cancer cell death (E) BEL No. 1

In one embodiment, a BEL with the following formula is within the scope of the of the present disclosure:

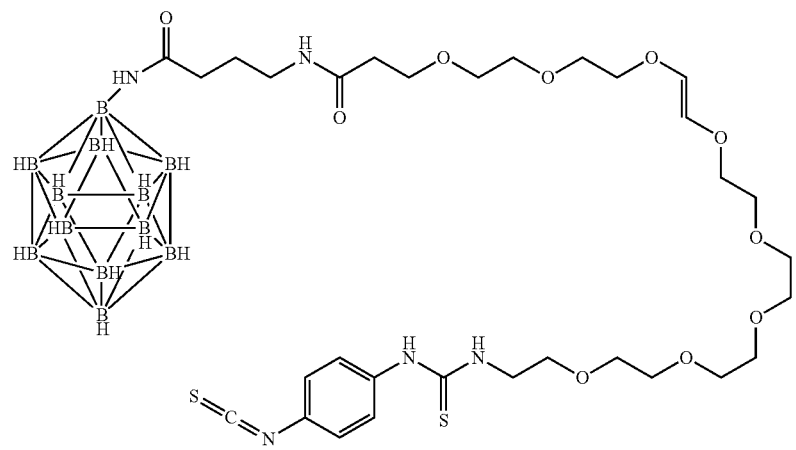

8: Target

It will be appreciated by one of ordinary skill in the art that BEL No. 1 is a precursor for more complex branched BELs. It is contemplated that BEL No. 1 is used to conjugate to a mAb of the invention to assess biochemical properties of ABCs which are contemplated herein. The estimated BAR is from 12-300 and more preferrably from 12-150.

(F) BEL No. 2

In one embodiment, a BEL with the following formula is within the scope of the of the present disclosure:

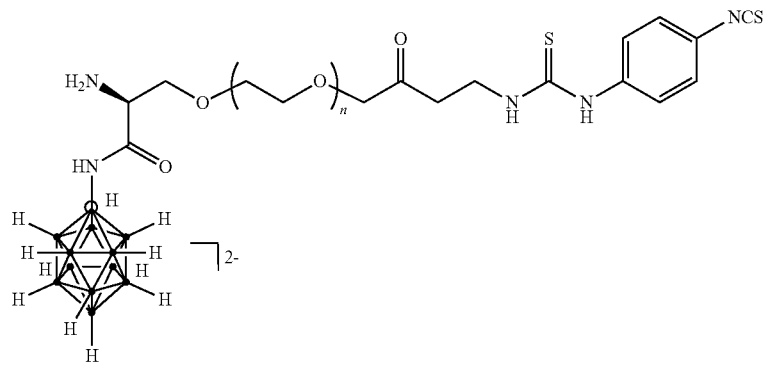

It will be appreciated by one of ordinary skill in the art that BEL No. 2 comprises a serine modification to BEL No. 1. It is contemplated that BEL No. 2 possesses zwitter-ion functionality due to a primary amine, which as will be appreciated by one of ordinary skill in the art may serve as a handle for a PET chelator. As will be appreciated by one of ordinary skill in the art, the introduction of the serine modification will pave the way for substantially higher BAR.

(G) BEL No. 3

In one embodiment, a BEL with the following formula is within the scope of the of the present disclosure:

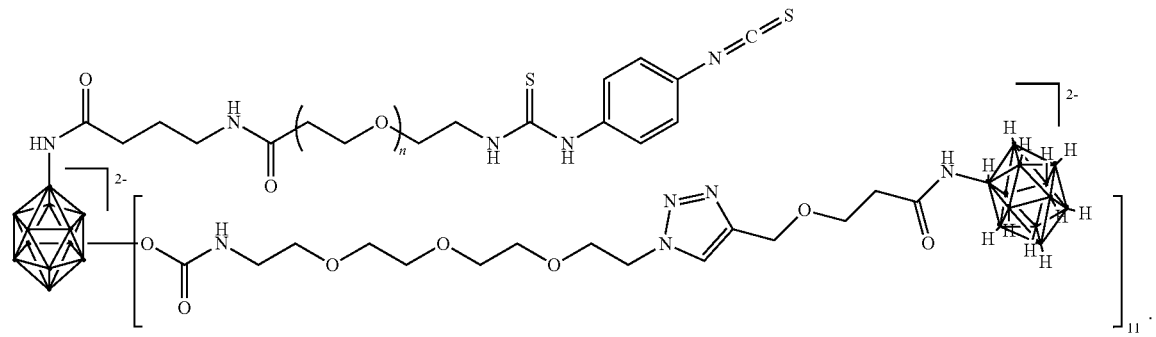

It will be appreciated by one of ordinary skill in the art that BEL No. 3 is a substantially more complex entity with n=11 pendant boron clusters. One of ordinary skill in the art will appreciate that in one embodiment n can equal 3-20 or more preferrably n=9-12. It is contemplated that BEL No. 3 is used to conjugate to a mAb of the invention to create an ABC utilized as a boron delivery vehicle for BNCT. The estimated BAR is from 144-1296 and more preferrably from 144-720.

V.) Boron Neutron Capture Therapy Using BELs

One aspect of the present disclosure is the use of BELs and ABCs as a modality for Boron Neutron Capture Therapy (BNCT). Briefly, BNCT is a binary treatment modality in which neither component alone is lethal or highly toxic. The two components comprise (i) the infusion or delivery of a capture compound, which preferentially is concentrated in the tumor, and (ii) the irradiation of the tumor site by neutrons. Given the large cross-section of thermal neutron interactions with $^{10}B$, there is consequently a high probability of a splitting of Boron nucleus into He and Li. Given that the ionization capability of He and Li is high, and the runs are short, then the cells preferably enriched by Boron are killed and the healthy cells are damaged much less. Given this, the advantage of BNCT is the destruction of tumor cells without a highly traumatic surgical procedure. However, as will be understood by one of skill in the art, success is predicated high concentration and selective localization of $^{10}B$ in tumor cells.

In one embodiment, $^{10}B$ is concentrated into a BEL of the invention and is conjugated to an antibody or fragment thereof to create an ABC. The ABC is then given to a patient and the BEL is localized into a tumor cell. The ABC containing $^{10}B$ are concentrated into the tumor and the tumor is irradiated using epithermal neutrons. The tumor cells are destroyed.

VI. Methods of Delivering BELs to a Cell

As will be appreciated by one of ordinary skill in the art, the ability to efficiently deliver high concentrations of Boron to a cell is an advantage of the present invention.

It is shown that the BELs of the present disclosure enables a higher amount of boron to be administered to a cell safely in mammals. Briefly, BELs of the disclosure are prepared as set forth in the disclosure. The BAR is pre-determined and the synthesis is set forth accordingly. The BEL is conjugated to an mAb of the invention using methods known in the art. The resulting ABC targets the antigen or antigen binding fragment and the boron is concentrated into a cancer cell.

Accordingly, it is shown that ABCs of the disclosure loaded with borons can be modified to selectively localize in high concentrations in tumor cells.

VII.) Kits/Articles of Manufacture

For use in the laboratory, prognostic, prophylactic, diagnostic and therapeutic applications described herein, kits are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise an ABC that is or can be detectably labeled and/or is loaded with a BEL of the disclosure. Kits can comprise a container comprising a drug unit. The kit can include all or part of the ABCs and/or BELs.

The kit of the invention will typically comprise the container described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a cancer or other immunological disorder.

The terms "kit" and "article of manufacture" can be used as synonyms.

In another embodiment of the invention, an article(s) of manufacture containing compositions, such as ABCc and/or BELs and/or ABCs loaded with BELs. The article of manufacture typically comprises at least one container and at least one label. Suitable containers include, for example, bottles, vials, syringes, and test tubes. The containers can be formed from a variety of materials such as glass, metal or plastic. The container can hold ABCs and/or BELs.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be an ABC loaded with a BEL.

The article of manufacture can further comprise a second container comprising a pharmaceutically-acceptable buffer, such as phosphate-buffered saline, Ringers solution and/or dextrose solution. It can further include other materials desirable from a commercial and user standpoint, including other buffers, diluents, filters, stirrers, needles, syringes, and/or package inserts with indications and/or instructions for use.

EXAMPLES

Various aspects of the invention are further described and illustrated by way of the several examples that follow, none of which is intended to limit the scope of the invention.

Example 1: Synthesis of BEL No. 1

Synthesis of 2: Ref. *J. Am. Chem. Soc.* 2013, 135, 13204. Compound 1 (10 g, 24.5 mmol, Strem Chemicals) in distilled $H_2O$ (70 mL) was heated at reflux to obtain clear solution. To this solution was added dropwise a solution of $H_2NOSO_3H$ (5.25 g, 46.4 mmol) in $H_2O$ (8 mL) over one (1) hr. The reaction was stirred at reflux for another three (3) hours and concentrated to 12 mL of volume. After keeping it in a refrigerator (4° C.) overnight, the formed solid was collected by filtration. The collected solid was washed with MeOH (16 mL×3), followed by acetonitrile (80 mL×2) to obtain Compound 2 (2.6 g, 32%, slightly better yield than the precious batch) as a white solid. LC-MS: tR 1.60 min; ES− 157 (M−1), 158, 159 with closo-Boron MS pattern.

Synthesis of 3: A borate Compound 2 (900 mg, 3.1 mmol: assumed as mono Cs salt) was dissolved in DMF (50 mL). To this was added NaH (496 mg of 60% in oil, 12.4 mmol) and heated at 50° C. for ~one (1) hour. Subsequently, to this solution was added pre-made Boc-GABA-OSu (1.2 g, 4.0 mmol) to heat at 50° C. overnight. After concentration, the resulting gum was dissolved in dichloromethane (~300 mL) and filtered. The filtrate was concentrated, washed with hexane and ethyl acetate several times to obtain Compound 3 (900 mg, 80% based on assumption of mono Na salt) as a pale yellow crystalline solid. LC-MS: ES− 343 (M+1) with closo-Boron MS pattern.

Synthesis of 4: To a stirred solution of Compound 3 (900 mg, 2.5 mmol: assumed as mono Na salt) in MeOH (20 mL) was slowly added 4M HCl/dioxane (4 mL/6 mL) at room temperature. After stirring at room temperature for five (5) hr., the solution was concentrated and washed with ethyl acetate to obtain Compound 4 (635 mg, 95% based on assumption of Na salt) as a thick pale yellow gel. LC-MS: ES− 243 (M+1) with closo-Boron MS pattern Synthesis of 5: A borate Compound 4 (250 mg, 0.95 mmol base on assumption of Na salt) was dissolved in acetonitrile (50 mL). To this was added triethylamine (280 uL, 2 mmol), followed by pre-made Boc-NH-PEG-OSu (690 mg, 1.08 mmol) to stir at room temperature for 24 hr. Completion of reaction was analyzed by LC-MS. After concentration, the resulting gum was dissolved in dichloromethane (~300 mL) and filtered. The filtrate was concentrated under vacuum, followed by washing with hexane/ethyl acetate and dried to obtain a gum. Crude was dissolved in MeOH (~7 mL) to purify by semi-prep HPLC (H2O:ACN:0.1% CH3COOH=0-100%) to obtain Compound 5 (380 mg, 41% based on the assumption of 2 equivalents of TEA salt). LC-MS: ES+ 767 (M+1) with closo-Boron MS pattern.

Synthesis of 6: To a stirred solution of Compound 5 (380 mg, 0.4 mmol based on the assumption of 2 equivalents of TEA salt) in MeOH (20 mL) was slowly added 4M HCl/dioxane (3 mL) at room temperature. After stirring at room temperature for one (1) hour, the solution was concentrated to provide Compound 6 (~300 mg+100 mg 2nd fraction, quantitative yield) as a pale yellow thick oil. LC-MS: ES− 667 (M+1) with closo-Boron MS pattern.

Synthesis of 8 (Target): To a solution of Compound 6 (300 mg, 0.34 mmol based on assumption of 2 equivalents of TEA salt) in i-PrOH 20 mL/H$_2$O 2.4 mL was added a solution of Compound 7 (346 mg, 1.8 mmol) in CHCl$_3$ (11 mL), followed by TEA (200 uL, 1.44 mmol). The resulting solution was stirred at room temperature overnight and concentrated under vacuum. LC-MS (ES+ 861, ES− 859 (M−1) with closo-Boron MS pattern. The crude was then washed with ethyl acetate (5 mL×3). The obtained precipitate was dissolved in acetonitrile to purify by using flash ISCO column chromatography (Column; 8 g of SiO$_2$:Eluents:DCM:MeOH=100:0 for 5 mins to 95:5 to gradually to 0:100 over 40 min.). The separated fractions of product were concentrated to obtain Compound 8 (126 mg, 25% based on assumption of six (6) equivalents of TEA salts) as yellowish-white semi-solid. LC/MS: tR 5.62 min. ES+ 860.7 (M+1), ES− 858.7 (M−1). HPLC: tR 4.39 min (95% pure): 1H NMR (CD3OD) δ 0.6-2 (br m baseline, BH's), 1.32 (t, CH3's of TEA), 1.80 (m, 2H, —CH2-), 2.04 (s), 2.50 (t, 2H), 2.75 (m, 2H), 3.26 (q, CH2 of TEA), 3.6-3.8 (br, —OCH2-, 36-40H), 7.2-7.6 (ABq, J=8 Hz, 4H). ("BEL No. 1"; Creagen Biosciences, Inc.). (FIG. 1).

BEL No. 1 has the following chemical structure:

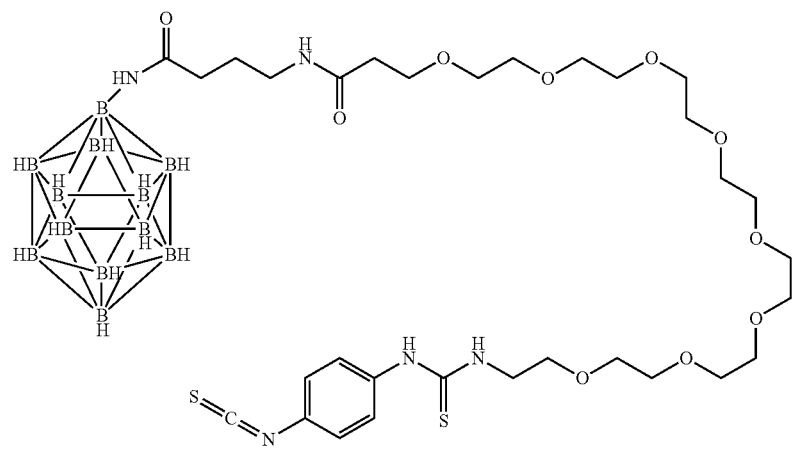

8: Target

Example 2: Synthesis of BEL No. 2

BEL No. 2 is synthesized in the following manner. Briefly, beginning with Ammonio-dodecahydro-closo-dodecaborate monoanion, Cs[closo-B12H11NH3] (1b). 1b is condensed with Fmoc-O-tBu-L-serine, which results in 2a, which is then followed by tert-Butyl deprotection by an appropriate method known in the art. See, for example, *J. Org. Chem.*, 2006, 71, 9045-9050) to yield closomer 2b.

Attendant to the foregoing, a Methyl-2-aminoethylketone derivative of phenyldiisothiocyanate (2c) is mixed with LDA in THF at −78 C to preform enolate. PEGn alcohol tosylate is then added to form adduct 2d.

2d and Fmoc-protected closomer 2b are condensed under Mitsunobu conditions to form closomer ether 2e. Fmoc deprotection is carried out using 5% DBU in 1-octanethiol/ethylacetate to yield 2f ("BEL No. 2").

BEL No. 2 has the following chemical structure:

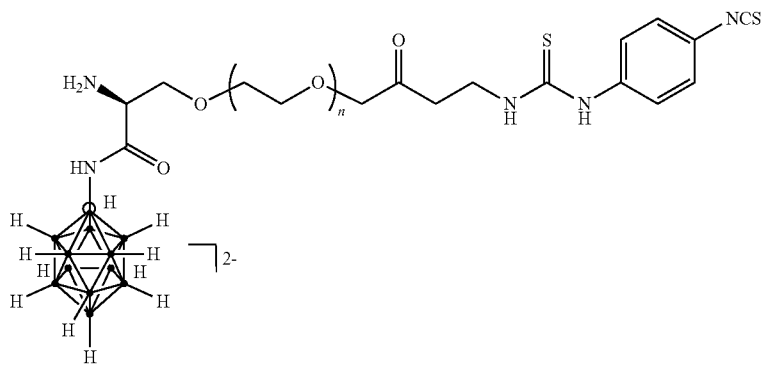

Example 3: Synthesis of BEL No. 3

BEL No. 3 is synthesized in the following manner. Briefly, N-Boc protected closomer 1c [$B_{12}NHCOCH_2CH_2CH_2NH$-Boc]$^{2-}$ was oxidized by refluxing in 30% $H_2O_2$ at 105° C., to install alcohol groups at all eleven (11) vertices. Alternatively, additional $H_2O_2$ may be added slowly to achieve the complete dissolution of 1c and this step is within the scope of the present disclosure. The resulting compound undecahydroxy-closo-dodecaborate (Cs$_2$3a) (3a) is confirmed by $^{11}$B NMR to contain only 1 signal. Additional $H_2O_2$ may be added followed by stirring at 105 C for up to thirteen (13) days. The resulting 3a is recovered as a Cs salt. See, BAYER, et. al., Inorg. Chem., vol. 43, No. 6 (2018-2020) (2004).

Then, The hydroxyl groups of 3a are firstly converted to 11-fold degenerate phenylcarbonate. Briefly, anhydrous pyridine (1 mol. eq.) is added slowly to a solution of 4-chloro-arylchloroformate (55 mol. eq) in anhydrous acetonitrile or pyridine (55 mol. eq.) and the reaction is heated to reflux temperature for 24 hours. The completion is confirmed by the appearance of a singlet in the $^{11}$B NMR spectrum near −17.4 ppm (approx. 24 hours). The reaction is filtered and the solvent is removed. The desired product is isolated using flash chromatography, isolating compound 3b.

Then, 3b (1 mol. eq.) is dissolved in acetonitrile (or anhydrous DMF) and 5 mol. eq of amino-PEG3 azide is added:

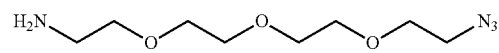

AZ101-100, Azido-PEG3-Amine; www.clickchemistrytools.com

The reaction is stirred at room temperature for six (6) days. Reaction mixture is concentrated on rotovap and the resulting residue is subjected to size exclusion chromatography over LH-20 using methanol as a solvent. The boron containing fractions are collected and solvent is removed on rotovap. See, SATISH, et. al., J. Am. Chem. Soc., 133(32) pp 12382-12385 (2011). The resulting compound is 3c.

Then, 1b (as Cs salt) is dissolved in dry acetonitrile and reacted with Propargyl-NHS Ester (3-Prop-2-ynyloxy-propionic acid NHS ester, using DBU as a catalyst:

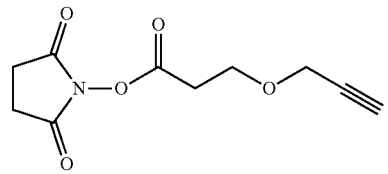

TA111, Propargyl-NHS Ester, www.clickchemistrytools.com

The reaction is carried out until 100% conversion occurred. The resulting compound is 3d.

Then 3c (1 mol. eq.) is dissolved in acetonitrile and mixed with 16 mol. eq. of 3d. TBTA as a DMSO solution (Sigman Aldrich, St. Louis, Mo.). Aminoguanidine (as aqueous solution) and CuSO$_4$ (0.4 mM final concentration) are pre-mixed and added to the reaction, followed by freshly prepared sodium ascorbate solution in water using methods known in the art to produce 3e.

Then 3e is subjected to four (4) steps: Boc-deprotection, followed by a reaction with free acid (Boc-N-amido-PEGn-acid, BP-21639 O-[2-(Boc-amino)ethyl]-Oμ-(2-carboxyethyl)polyethylene glycol, followed by Boc-deprotection to yield a free amine. The resulting free amino-compound is reacted with p-phenylene diisothiocyanate (Sigman Aldrich, St. Louis, Mo.) in dry acetonitrile at elevated temperature to give 3f ("BEL No. 3")

BEL No. 3 has the following chemical structure:

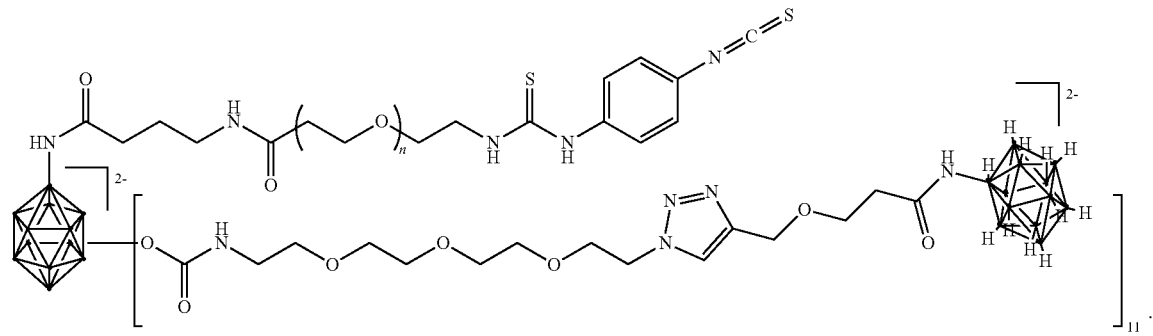

Example 4: Characterization of Antibodies Used to Form an Antibody Boron Conjugate ("ABC")

Two (2) commercially available antibodies used in obtaining the ABC were Trastuzumab and Cetuximab. Briefly, Trastuzumab is a humanized IgG1 that binds HER2/neu (ErbB2) and is overexpressed on breast and gastric carcinomas and on brain metastases that have arisen from breast cancer. Additionally, Cetuximab is a chimeric IgG1 that is binds wild type EGFR and blocks downstream receptor signaling. EGFR is overexpressed in a variety of solid tumors including non-small cell lung cancer and a variety of head and neck carcinomas, as well as colon cancer. Both antibodies are rapidly internalized upon binding to their cognate target and are suitable for delivering the boron-containing payload to cells.

To confirm the binding of Trastuzumab and Cetuximab, assays were performed using standard methods. The results confirm binding of Trastuzumab and Cetuximab to four (4) cancer cell lines (NCL N87, HCC1954, MDA-MB-453, and MDA-MB-468) and shows that three (3) out of four (4) chosen cell lines have a high level of expression of Her2/neu or EGFR, respectively. (FIG. 5).

Example 5: Generation of an Antibody Boron Conjugate ("ABC") Comprising BEL No. 1

An ABC was produced by conjugation of an antibody (mAb) to BEL No. 1 using the following concept and design. A general schematic of an ABC set forth in this disclosure is set forth below:

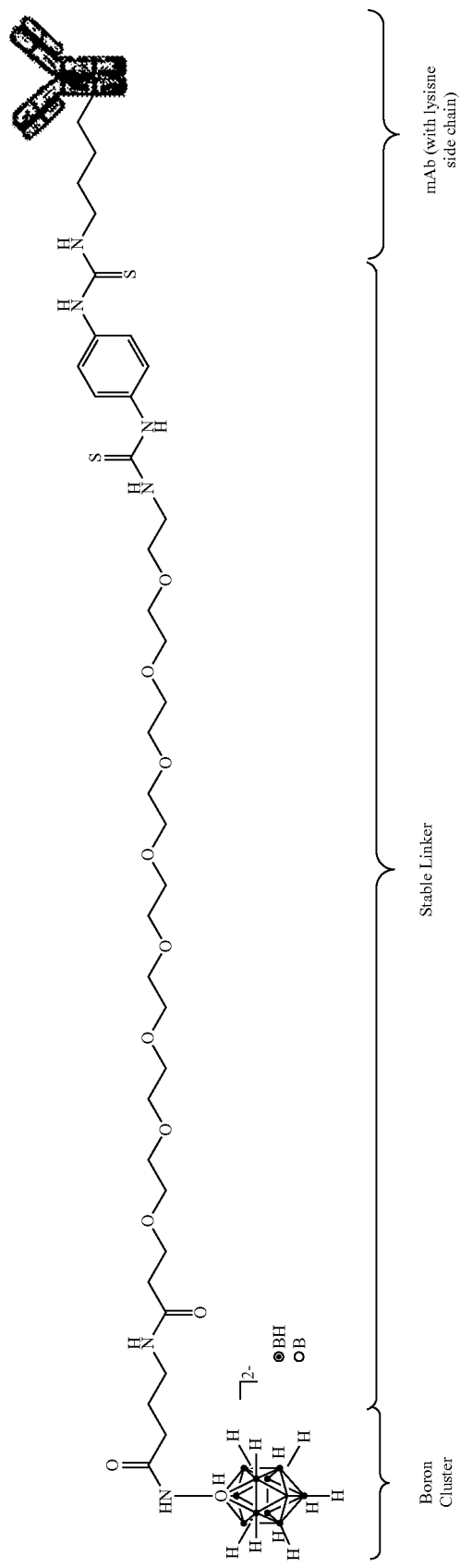

Using the following protocol, an ABC comprising BEL No. 1 was produced. Briefly, an antibody is buffer exchanged into sodium borate/NaCl buffer pH 8.9. Then, the BEL No. 1 linker solution in DMSO is added at ratios ranging from 5 to 40 BEL No. 1/mAb (mole/mole). The reaction is stirred at 35° C. for 2-3 hours. The resulting conjugate is purified into histidine formulation buffer (pH6) using PD-10 or similar desalting column and analyzed for boron/mAb ratio, aggregation, and the binding affinity using the unconjugated antibody as a control.

Example 6: Method of Determining a Boron to Antibody (BAR) of an ABC Comprising BEL No. 1

To determine the BAR of an ABC comprising BEL No. 1, the following ICP OES procedure was used. Briefly, 10 and 20 μL of BEL No. 1-Trastuzumab and BEL No. 1-Cetuximab were diluted with 5 mL of 10% Nitric Acid. The boron content in each sample was then measured on an Agilent 5110 ICP-OES using an Agilent SPS4 Autosampler for sample introduction. The data was analyzed using Agilent's ICP Expert Software, version 7.4.2.10790. Boron was measured axially at the 249.772 nm wavelength and the internal standard Beryllium was measured axially at the 313.042 nm wavelength. Beryllium was tested into the solution at 1:5 the flowrate before introduction to the spray chamber. A standard curve using 1000, 100, 10, 1 and 0 ppb of boron was used to calculate the concentration of boron in each sample. The Results are set forth in FIG. 6.

Example 7: Characterization of the BEL No. 1-Trastuzumab ABC

To confirm the molecular mass and the distribution of conjugated heavy chain ("HC") and light chain ("LC") of the BEL No. 1-Trastuzumab ABC an LCMS the conjugate was reduced and subject to mass analysis by LCMS without de-glycosylation. Briefly, the samples were prepared by adding 1/20 the volume of 200 mM DTT and incubating at 37° C. for one (1) hour. Samples were analyzed using an Agilent 1260 LC and an Agilent 6520 QTOF mass spectrometer. The LC column was a 2 mm ID×10 cm long column packed with 10 μm PLRPS polystyrene reverse phase packing. The solvents were 0.1% formic acid in water (A) and 0.1% formic acid in acetonitrile (B). The gradient was a one (1) minute hold a 1% B, a fourteen (14) minute ramp to 70% B, one (1) minute ramp to 90% B, one (1) minute hold at 90% B, and (one) 1 minute ramp back to 1% B. Data was acquired using Agilent Mass Hunter Data Acquisition software and analyzed using Agilent Mass Hunter Qualitative Analysis with Bioconfirm. Deconvolution used the Maximum Entropy model.

The results show that the correct and expected mass of 860 Da for BEL No. 1 was confirmed for the representative ABC. Furthermore, the abundance of conjugated HC and LC is 40% and 20%, respectively, in case for the low substitution BEL No. 1 (FIG. 7). Due to a lack of sample deglycosylation, reconciliation of the predicted and observed molecular masses was necessary and is set forth in FIG. 8A.

Example 8: Binding Affinity of the ABC by ELISA

To test whether conjugation of BEL No. 1 through lysine side chain perturbes the ability of the ABC to bind its cognate cellular target, in particular for highly substituted ABC, binding ELISA was performed. Briefly, the plate was coated with recombinant human Her2/ERBB2 Protein as His-Tag (Sino cat #10004-H08H) or recombinant human EGFR Protein also as His-Tag (Sino cat #10001H08B) at 1 μg/ml, 50 μl/well, 4° C. overnight. The plate was then washed three (3) times and blocked by adding 1% of BSA PBS-T 150 μl/well blocking solution. The blocking solution was left on the plate for one (1) hr. at room temperature. Antibodies or ABCs were serially diluted starting from 0.5 μg/ml followed by the 1 to 3 dilution to generate a total of 11 concentrations in 50 μL per well. The antibody was allowed to incubated for two (2) hrs at room temperature. The unbound antibody was then washed 3 times. The bound antibody was detected as follows: Secondary Ab: Goat anti-hIgG Fc-HRP (Jackson Immuno) cat #109-035-098 diluted at 1:10,000 in the total volume 50 μl/well, incubated at RT for 1 hr. Detection reagent: TMB (BioFx, cat # TTMB-0100-01) at 70 μl/well incubated at room temperature for twenty (20) minutes. The stop solution: BioFX cat # LBS-0100-01 at 50 ul/well.

The plate was read using Cytation 1 (Thermo-Fisher) microplate reader at 650 nm. The results show that conjugation did not affect the binding affinity of the ABC at the low substitution ratio. (FIG. 9). Furthermore, FIG. 10 shows that similar to the ABC conjugates with low degree of substitution, the highly substituted conjugates did not show any decrease in the binding affinity and displayed nearly superimposable titration curves. The results confirmed that the binding affinities for the highly substituted conjugates are similar to that of the positive control mAb. Also noted is that the negative control (e.g. isotype control) does not bind under these conditions.

Example 9: Boron Uptake Study Utilizing High Boron Loaded ABCs

To determine whether the ABCs can deliver boron to antigen positive cancer cells, a boron uptake study was performed using the following protocols. Briefly, the cells were exposed to ABC (20 μg/mL) for 2 hours, then washed 3× times and processed. The results show that boron is delivered to cells in a selective manner since there was no uptake in the antigen negative cells (results not shown) and the amount of boron uptake correlates with the BAR. The highest uptake was seen in MDA-MB-468 followed by A431 cell line. HCC1954 cell line had the lowest uptake values. The measured boron was in concord with the amount of the internalized antibody component of the ABC that was determined by ELISA. MDA-MB-468 cell line has the highest rate of internalization (data not shown) that is in agreement with the above results. (FIG. 11).

Example 10: Human Clinical Trials for the Treatment of Human Carcinomas Through the Use of ABCs Loaded with BELs ABCs loaded with BELs are used in accordance with the present invention which specifically accumulate in a tumor cell, and are used in the treatment of certain tumors and other immunological disorders and/or other diseases. In connection with each of these indications, two clinical approaches are successfully pursued.

I.) Adjunctive Therapy:

In adjunctive therapy, patients are treated with ABCs loaded with BELs in combination with a chemotherapeutic or pharmaceutical or biopharmaceutical agent or a combination thereof. Primary cancer targets, are treated under standard protocols by the addition of ABCs loaded with BELs and then irradiated. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents. These dosage reductions allow additional and/or prolonged therapy by reducing dose-related toxicity of the chemotherapeutic or biologic agent.

II.) Monotherapy:

In connection with the use of the ABCs loaded with BELs in monotherapy of tumors, the ABCs loaded with BELs are administered to patients without a chemotherapeutic or pharmaceutical or biological agent. In one embodiment, monotherapy is conducted clinically in end-stage cancer patients with extensive metastatic disease. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents.

Dosage

Dosage regimens may be adjusted to provide the optimum desired response. For example, a single ABC injection of loaded BELs may be administered, several divided doses may be administered over time or the dose may be proportionally reduced or increased as indicated by the exigencies of the therapeutic situation. "Dosage Unit Form" as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the ABC loaded with the BEL, the individual mechanics of the irradiation mechanism (reactor) and the particular therapeutic or prophylactic effect to be achieved, and (b) the limitations inherent in the art of compounding such an compound for the treatment of sensitivity in individuals.

Clinical Development Plan (CDP)

The CDP follows and develops treatments of using ABCs loaded with BELs which are then irradiated using Neutron Capture Therapy in connection with adjunctive therapy or monotherapy. Trials initially demonstrate safety and thereafter confirm efficacy in repeat doses. Trials are open label comparing standard chemotherapy with standard therapy plus ABCs loaded with BELs which are then irradiated using Boron Neutron Capture Therapy. As will be appreciated, one non-limiting criteria that can be utilized in connection with enrollment of patients is concentration of BELs in a tumor as determined by standard detection methods known in the art.

The present invention is not to be limited in scope by the embodiments disclosed herein, which are intended as single illustrations of individual aspects of the invention, and any that are functionally equivalent are within the scope of the invention. Various modifications to the models, methods, and life cycle methodology of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE I

Examples of Boron Clusters used to synthesize Boron Enriched Linkers.

| Number of Vertices | Polyhedron |
| --- | --- |
| 4 | Tetrahedron |
| 5 | Trigonal bipyramid |
| 6 | Octahedron |
| 7 | Pentagonal bipyramid |
| 8 | $D_{2d}$ (trigonal) dodecahedron |
| 9 | Tricapped trigonal prim |
| 10 | Bicapped square antiprism |
| 11 | Edge-contracted icosahedron |
| 12 | Icosahedron |

TABLE I(A)

The 4n rules are enumerated in the following table.

| Electron count | Name | Predicted structure |
| --- | --- | --- |
| 4n − 2 | Bicapped closo | n − 2 vertex closo polyhedron with 2 capped (augmented) faces |
| 4n | Capped closo | n − 1 vertex closo polyhedron with 1 face capped |
| 4n + 2 | closo | closo polyhedron with n vertices |
| 4n + 4 | nido | n + 1 vertex closo polyhedron with 1 missing vertex |
| 4n + 6 | arachno | n + 2 vertex closo polyhedron with 2 missing vertices |
| 4n + 8 | hypho | n + 3 vertex closo polyhedron with 3 missing vertices |
| 4n + 10 | klado | n + 4 vertex closo polyhedron with 4 missing vertices |

The invention claimed is:

1. A composition comprising a chemical structure of the following formula:

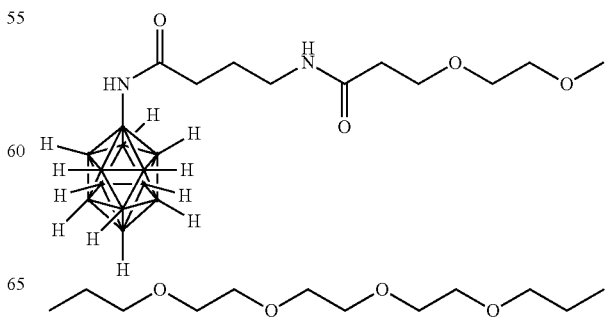

-continued

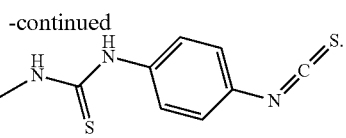

2. The composition of claim 1, wherein the composition is conjugated to an antibody.

3. An article of manufacture comprising the composition of claim 1.

4. An Antibody Boron Conjugate (ABC) comprising,
   a. an antibody; and
   b. a boron enriched linker (BEL), wherein said BEL is conjugated to said antibody, and wherein the BEL comprises a chemical structure of the following formula:

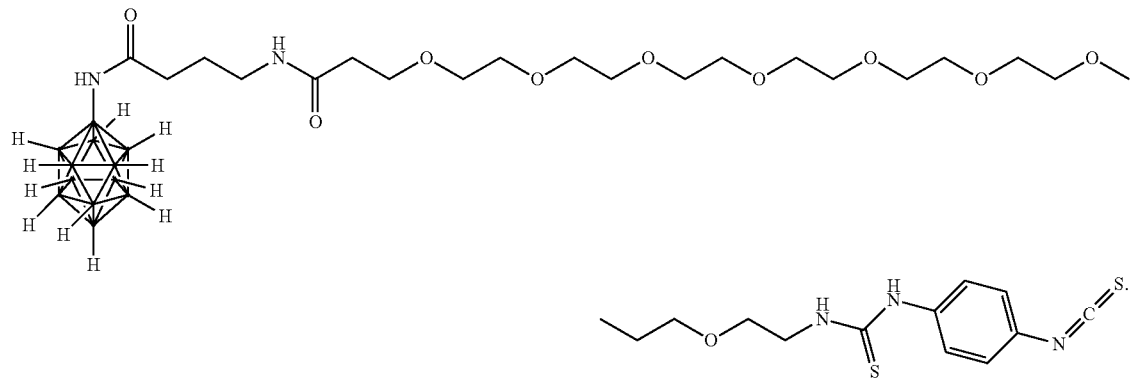

5. The ABC of claim 4, wherein the boron antibody ratio (BAR) is from 24-400.

6. The ABC of claim 4, further comprising a stretcher unit.

7. The ABC of claim 4, further comprising a spacer unit.

8. The ABC of claim 4, further comprising a bio-conjugation handle.

9. The ABC of claim 4, wherein the antibody binds to EGFR.

10. The ABC of claim 4, wherein the antibody binds to HER2/neu (ErbB2).

11. An article of manufacture comprising the ABC of claim 4.

12. A method of performing Neutron Capture Therapy in the treatment of human cancer comprising:
   a. conjugating a composition of claim 1 with an antibody to create an antibody boron conjugate ABC;
   b. injecting the ABC into a tumor, whereby said composition accumulates into a tumor cell; and
   c. irradiating the accumulated composition with neutrons.

13. The method of claim 12, wherein the irradiation comprises epithermal neutrons.

14. The method of claim 12, wherein the irradiation triggers neutron activation.

15. The method of claim 12, wherein the antibody binds EGFR.

16. The methods of claim 12, wherein the antibody binds HER2/neu.

17. The method of claim 12, wherein the cancer is selected from the group consisting of breast cancer, brain cancer, gastric cancer, lung cancer, colon cancer, and head and neck cancer.

* * * * *